(12) United States Patent
Hicks et al.

(10) Patent No.: US 10,520,446 B2
(45) Date of Patent: Dec. 31, 2019

(54) POLYMER MATERIALS

(71) Applicants: Smith & Nephew PLC, Watford, Hertfordshire (GB); University of Sheffield, Sheffield (GB)

(72) Inventors: John Kenneth Hicks, York (GB); Stephen Rimmer, Sheffield (GB); Dorothy McCulloch, York (GB); Richard Hoskins, York (GB)

(73) Assignees: Smith & Nephew PLC, Watford (GB); University of Sheffield, Sheffield (GB)

( * ) Notice: Subject to any disclaimer, the term of this patent is extended or adjusted under 35 U.S.C. 154(b) by 0 days.

(21) Appl. No.: 15/325,070

(22) PCT Filed: Jul. 3, 2015

(86) PCT No.: PCT/EP2015/065234
§ 371 (c)(1),
(2) Date: Jan. 9, 2017

(87) PCT Pub. No.: WO2016/005288
PCT Pub. Date: Jan. 14, 2016

(65) Prior Publication Data
US 2017/0183705 A1    Jun. 29, 2017

(30) Foreign Application Priority Data

| Jul. 10, 2014 | (GB) | ................................. | 1412332.7 |
| Jul. 10, 2014 | (GB) | ................................. | 1412345.9 |
| Jul. 10, 2014 | (GB) | ................................. | 1412427.5 |
| Apr. 16, 2015 | (GB) | ................................. | 1506451.2 |
| Apr. 16, 2015 | (GB) | ................................. | 1506453.8 |
| Apr. 16, 2015 | (GB) | ................................. | 1506463.7 |

(51) Int. Cl.
| C12Q 1/18 | (2006.01) |
| G01N 21/77 | (2006.01) |
| A61L 15/26 | (2006.01) |
| A61L 15/42 | (2006.01) |
| C08L 75/02 | (2006.01) |
| C08L 33/26 | (2006.01) |
| G01N 21/78 | (2006.01) |
| A61L 15/58 | (2006.01) |
| C08F 220/56 | (2006.01) |
| G01N 33/569 | (2006.01) |

(52) U.S. Cl.
CPC .............. *G01N 21/78* (2013.01); *A61L 15/26* (2013.01); *A61L 15/425* (2013.01); *A61L 15/58* (2013.01); *C08F 220/56* (2013.01); *C08L 33/26* (2013.01); *C08L 75/02* (2013.01); *C12Q 1/18* (2013.01); *G01N 21/77* (2013.01); *G01N 33/56911* (2013.01); *G01N 33/56938* (2013.01); *C08L 2205/04* (2013.01); *G01N 2333/21* (2013.01); *G01N 2333/31* (2013.01); *G01N 2800/26* (2013.01)

(58) Field of Classification Search
None
See application file for complete search history.

(56) References Cited

U.S. PATENT DOCUMENTS

| 2,249,867 | A | 7/1941 | Snelling |
| 3,675,654 | A | 7/1972 | Baker et al. |
| 3,759,261 | A | 9/1973 | Wang |
| 4,029,598 | A | 6/1977 | Neisius et al. |
| 4,192,311 | A | 3/1980 | Felfoldi |
| 4,382,380 | A | 5/1983 | Martin |
| 4,705,513 | A | 11/1987 | Sheldon et al. |
| 4,728,499 | A | 3/1988 | Fehder |
| 4,813,942 | A | 3/1989 | Alvarez |
| 4,885,077 | A | 12/1989 | Karakelle et al. |
| 4,999,306 | A | 3/1991 | Yafuso et al. |
| 5,104,660 | A | 4/1992 | Chvapil et al. |
| 5,181,905 | A | 1/1993 | Flam |
| 5,277,872 | A | 1/1994 | Bankert et al. |

(Continued)

FOREIGN PATENT DOCUMENTS

| AU | 2003204827 | 5/2006 |
| CN | 100484501 | 5/2009 |

(Continued)

OTHER PUBLICATIONS

Dargaville, Tim R; et al; "Sensors and imaging for wound healing: A review" Biosensors and Bioelectronics, 41, 30-42, 2013 (Year: 2013).*

(Continued)

*Primary Examiner* — David W Berke-Schlessel
(74) *Attorney, Agent, or Firm* — Knobbe, Martens, Olson & Bear LLP

(57) ABSTRACT

A polyurethane material for the detection or sensing of species or stimulus comprising a polyurethane network
comprising immobilized therein, or modified by the immobilization therein of,
a hydrophilic polymer comprising a ligand or moiety for the detection or sensing of species or stimulus
and an indicator for indicating detection or sensing
wherein species or stimulus is selected from chemical or biological species or stimulus; the material for medical, dental, hygiene, point of use sterilization, sanitation, personal care, biosurveillance or packaging use, the use thereof preferably for detecting and/or sensing or binding bacteria, or for detecting or sensing pH or for detection or scanning with use of a reader; a Kit and a device comprising the same; and a process for the preparation thereof.

12 Claims, 11 Drawing Sheets

(56) References Cited

U.S. PATENT DOCUMENTS

| | | | |
|---|---|---|---|
| 5,536,783 A | 7/1996 | Olstein et al. |
| 5,571,684 A | 11/1996 | Lawrence et al. |
| 5,690,624 A | 11/1997 | Sasaki et al. |
| 5,766,212 A | 6/1998 | Jitoe et al. |
| 5,788,687 A | 8/1998 | Batich et al. |
| 5,852,126 A | 12/1998 | Barnard et al. |
| 5,853,669 A | 12/1998 | Wolfbeis |
| 5,897,516 A | 4/1999 | Kadash et al. |
| 6,120,904 A | 9/2000 | Hostettler et al. |
| 6,284,942 B1 | 9/2001 | Rabin |
| 6,333,093 B1 | 12/2001 | Burrell et al. |
| 6,388,043 B1 | 5/2002 | Langer et al. |
| 6,482,491 B1 | 11/2002 | Samuelsen et al. |
| 6,617,488 B1 | 9/2003 | Springer et al. |
| 6,688,525 B1 | 2/2004 | Nelson et al. |
| 6,696,240 B1 | 2/2004 | Kloepfer et al. |
| 6,747,185 B2 | 6/2004 | Inoue et al. |
| 6,772,708 B2 | 8/2004 | Klofta et al. |
| 6,815,207 B2 | 11/2004 | Yabuki et al. |
| 7,159,532 B2 | 1/2007 | Klofta et al. |
| 7,605,298 B2 | 10/2009 | Bechert et al. |
| 7,622,629 B2 | 11/2009 | Aail |
| 7,749,531 B2 | 7/2010 | Booher |
| 7,777,092 B2 | 8/2010 | Lykke et al. |
| 7,873,141 B2 | 1/2011 | Imai et al. |
| 8,372,049 B2 | 2/2013 | Jaeb et al. |
| 8,425,996 B2 | 4/2013 | Gorski et al. |
| 8,791,315 B2 | 7/2014 | Lattimore et al. |
| 8,795,257 B2 | 8/2014 | Coulthard et al. |
| 8,896,706 B2 | 11/2014 | van den Hengel et al. |
| 8,927,801 B2 | 1/2015 | Klofta |
| 8,997,682 B1 | 4/2015 | Ashcroft |
| 9,311,520 B2 | 4/2016 | Burg et al. |
| 9,445,749 B2 | 9/2016 | Erickson et al. |
| 9,504,421 B2 | 11/2016 | Greener |
| 9,829,471 B2 | 11/2017 | Hammond et al. |
| 10,053,532 B2 | 8/2018 | Hanson et al. |
| 2002/0062114 A1 | 5/2002 | Murai et al. |
| 2002/0091347 A1 | 7/2002 | Eakin |
| 2004/0044299 A1 | 3/2004 | Utsugi |
| 2004/0133090 A1 | 7/2004 | Dostoinov et al. |
| 2005/0105789 A1 | 5/2005 | Isaacs et al. |
| 2005/0187146 A1 | 8/2005 | Helmus et al. |
| 2005/0199055 A1 | 9/2005 | Browne |
| 2006/0140999 A1 | 6/2006 | Lendlein et al. |
| 2007/0048224 A1 | 3/2007 | Howell et al. |
| 2007/0129784 A1 | 6/2007 | Lendlein et al. |
| 2007/0142762 A1 | 6/2007 | Kaplan et al. |
| 2007/0188759 A1 | 8/2007 | Mehendale et al. |
| 2007/0225663 A1 | 9/2007 | Watt et al. |
| 2007/0270774 A1 | 11/2007 | Bergman et al. |
| 2007/0276207 A1 | 11/2007 | Eagland et al. |
| 2008/0021166 A1 | 1/2008 | Tong et al. |
| 2008/0208151 A1 | 8/2008 | Zacharias et al. |
| 2009/0062757 A1 | 3/2009 | Long et al. |
| 2009/0157024 A1 | 6/2009 | Song |
| 2009/0190135 A1 | 7/2009 | Clarizia et al. |
| 2009/0198167 A1 | 8/2009 | Ambrosio |
| 2009/0216168 A1 | 8/2009 | Eckstein et al. |
| 2009/0221977 A1 | 9/2009 | Blott et al. |
| 2010/0041968 A1 | 2/2010 | Meschisen et al. |
| 2010/0069838 A1 | 3/2010 | Weber et al. |
| 2010/0112680 A1 | 5/2010 | Brockwell et al. |
| 2010/0168695 A1 | 7/2010 | Robles et al. |
| 2010/0168700 A1 | 7/2010 | Schmidt et al. |
| 2010/0178203 A1 | 7/2010 | Kane et al. |
| 2011/0274593 A1 | 11/2011 | Gorski et al. |
| 2012/0123220 A1 | 5/2012 | Iyer et al. |
| 2012/0201437 A1 | 8/2012 | Ohnemus |
| 2012/0215190 A1 | 8/2012 | Kawashima |
| 2012/0256750 A1 | 10/2012 | Novak |
| 2012/0264163 A1 | 10/2012 | Booher |
| 2012/0279101 A1 | 11/2012 | Pretsch et al. |
| 2012/0323274 A1 | 12/2012 | Lendlein et al. |
| 2013/0066285 A1 | 3/2013 | Locke et al. |
| 2013/0066289 A1 | 3/2013 | Song et al. |
| 2013/0087298 A1 | 4/2013 | Phillips et al. |
| 2013/0131621 A1 | 5/2013 | Van Holten et al. |
| 2013/0303865 A1 | 11/2013 | Rebec et al. |
| 2014/0098209 A1 | 4/2014 | Neff |
| 2014/0121487 A1 | 5/2014 | Faybishenko et al. |
| 2014/0138441 A1 | 5/2014 | Davalos et al. |
| 2014/0154789 A1 | 6/2014 | Polwart et al. |
| 2014/0296808 A1 | 10/2014 | Curran et al. |
| 2015/0055134 A1 | 2/2015 | Papautsky et al. |
| 2015/0080685 A1 | 3/2015 | Markle et al. |
| 2015/0246995 A1 | 9/2015 | Hanson et al. |
| 2015/0265743 A1 | 9/2015 | Hanson et al. |
| 2015/0351970 A1 | 12/2015 | Dagger et al. |
| 2016/0100987 A1 | 4/2016 | Hartwell et al. |
| 2016/0262672 A1 | 9/2016 | Hammond et al. |
| 2016/0346421 A1 | 12/2016 | Courage et al. |
| 2017/0000407 A1 | 1/2017 | Saxby et al. |
| 2018/0196021 A1 | 7/2018 | Hammond et al. |

FOREIGN PATENT DOCUMENTS

| | | |
|---|---|---|
| CN | 101453969 | 6/2009 |
| CN | 101490556 | 7/2009 |
| CN | 201414880 | 3/2010 |
| CN | 101894212 | 11/2010 |
| CN | 102879393 | 1/2013 |
| CN | 103217503 | 7/2013 |
| EP | 0 340 018 | 11/1989 |
| EP | 0 430 608 | 6/1991 |
| GB | 905040 | 9/1962 |
| GB | 1255395 | 12/1971 |
| JP | S54-176283 | 12/1979 |
| JP | S57-162304 | 10/1982 |
| JP | H07-055788 | 3/1995 |
| JP | 2002-165757 | 6/2002 |
| JP | 2006-338521 | 12/2006 |
| JP | 2007-163350 | 6/2007 |
| JP | 2012-157438 | 8/2012 |
| KR | 10 2006 0133139 | 12/2006 |
| KR | 20120059006 | 6/2012 |
| RU | 114854 | 4/2012 |
| WO | WO 1983/00742 | 3/1983 |
| WO | WO 1998/12996 | 4/1998 |
| WO | WO 1999/12581 | 3/1999 |
| WO | WO 2002/047737 | 6/2002 |
| WO | WO 2005/052572 | 6/2005 |
| WO | WO 2006/042871 | 4/2006 |
| WO | WO 2006/110502 | 10/2006 |
| WO | WO 2006/133430 | 12/2006 |
| WO | WO 2008/125995 | 10/2008 |
| WO | WO 2011/098575 | 8/2011 |
| WO | WO 2012/074509 | 6/2012 |
| WO | WO 2012/131386 | 10/2012 |
| WO | WO 2013/074509 | 5/2013 |
| WO | WO 2014/066913 | 5/2014 |
| WO | WO 2014/113770 | 7/2014 |
| WO | WO 2016/005288 | 1/2016 |

OTHER PUBLICATIONS

Chen et al., "A PNIPAM-based fluorescent nanothermometer with ratiometric readout", Chemical Communications, vol. 47, No. 3, Nov. 26, 2010 pp. 994-996.

Reddy et al., "Synthesis and characterization of semi-interpenetrating polymer networks based on polyurethane and N-isopropylacrylamide for wound dressing", Journal of Biomedical Materials Research Part B: Applied Biomaterials, vol. 88B, No. 1, Sep. 8, 2008, pp. 32-40.

Uchiyama et al., "Fluorescent molecular thermometers based on polymers showing temperature-induced phase transitions and labeled with polarity-responsive benzofurazans", Analytical Chemistry, American Chemical Society, vol. 75, No. 21, Oct. 4, 2003, pp. 5926-5935.

International Search Report and Written Opinion, re PCT Application No. PCT/EP2015/065234, dated Oct. 12, 2015.

International Preliminary Report on Patentability, re PCT Application No. PCT/EP2015/065234, dated Jan. 19, 2017.

(56) References Cited

OTHER PUBLICATIONS

Mohr, G. et al., "Design of acidochromic dyes for facile preparation of pH sensor layers", Anal Bioanal Chem, vol. 392, pp. 1411-1418, in 8 pages.
Loh, B.Y. et al., "Automated Mobile pH Reader on a Camera Phone", IAENG International Journal of Computer Science, vol. 38(3), Aug. 2011, in 7 pages.
Trupp, S., "Development of pH-sensitive indicator dyes for the preparation of micro-patterned optical sensor layers", Sensors and Actuators B, vol. 150, Jul. 15, 2010, pp. 206-210, in 5 pages.
Cho, S.M. et al., "Thermo-sensitive hydrogels based on interpenetrating polymer networks made of poly(N-isopropylacrylamide) and polyurethane", Journal of Biomaterials Science, vol. 21 (8-9), 2010, pp. 1051-1068, in 18 pages.

\* cited by examiner

Figure 3 Synthesis of highly branched poly(N-isopropylacrylamide) and three step chain end modification to attach vancomycin. Stepwise from N-*iso*propyl acrylamide to highly branched Pyrrole ended polymer, Acid ended polymer, NHS-Succinimide ended polymer and then vancomycin (labelled as R) ended polymer.

Shift in peak fluorescence emission wavelength (average mean of distribution) of vancomycin derived extended poly(NIPAM-co-NRA-block-NIPAM) (XBI, black), poly(NIPAM-block-NIPAM-co-NRA) (XBO, clear) samples compared to poly(NIPAM-co-NRA) (grey).

Figure 5
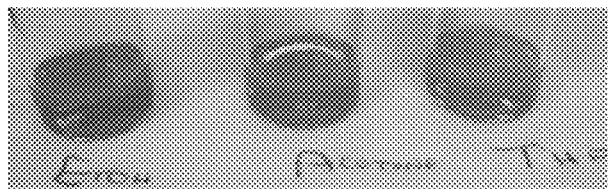
Sample 3.1.1 in ethanol, acetone and THF
Figure 6
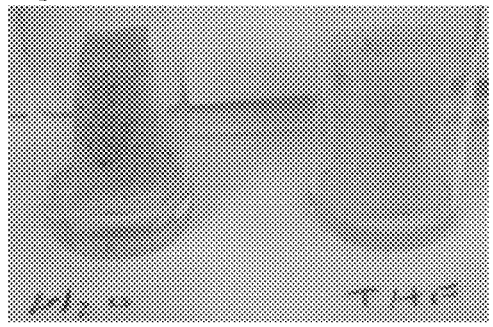
Sample 3.1.1 in deionised water and THF
Figure 7 Light microscope images of HBPNIPAM/Polymyxin copolymer foam 3.3.2
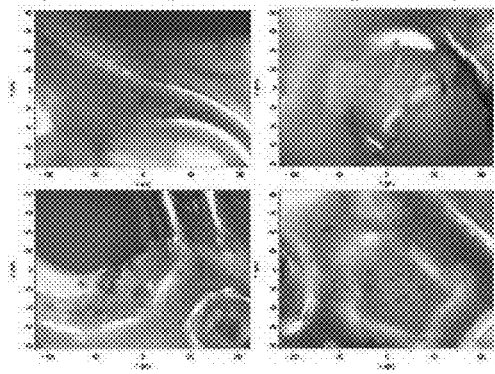
Figure 8 25:1 P-NIPAM/Van/NR 4%wt PU, washed 5x
Figure 9 25:1 P-NIPAM/van NR 10wt% PU, washed 5x
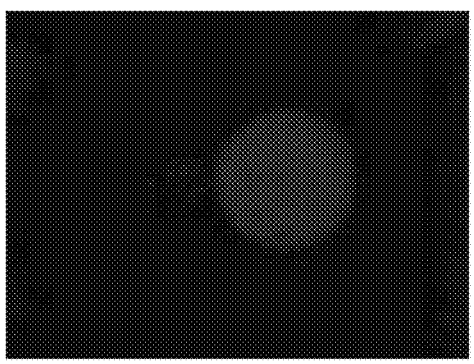
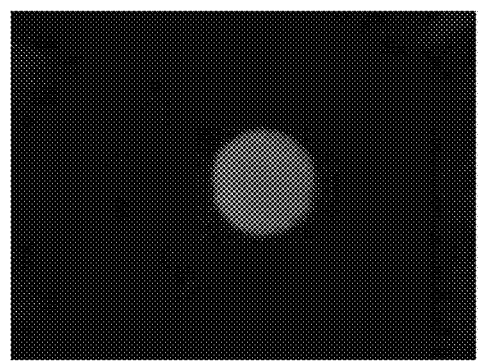

Figure 10 Distribution of polymer in foam
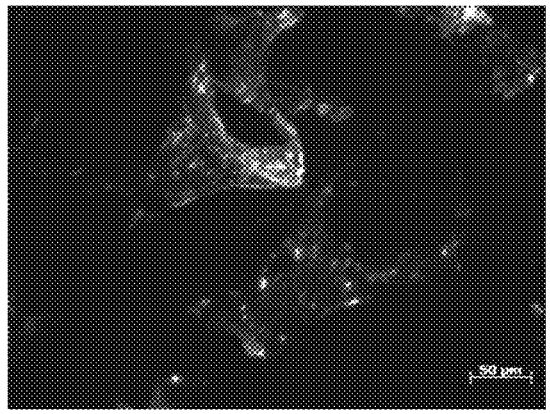
Figure 11 cold (control)   Figure 12 warm   Figure 13 hot
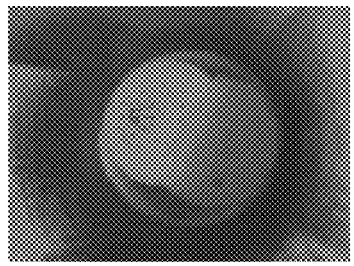 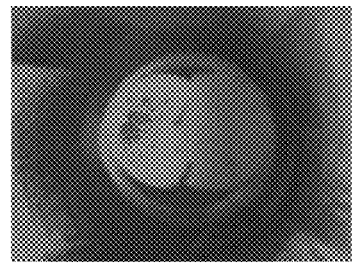 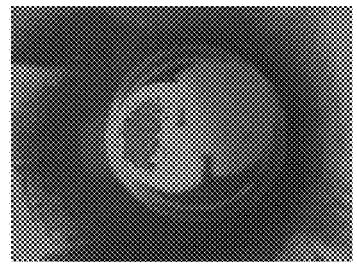
Figure 14 Fluorescent activity of dressing comprising polymer in PU foam supported on adhesive film
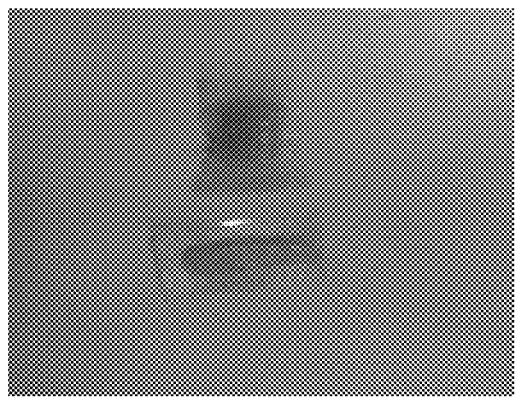 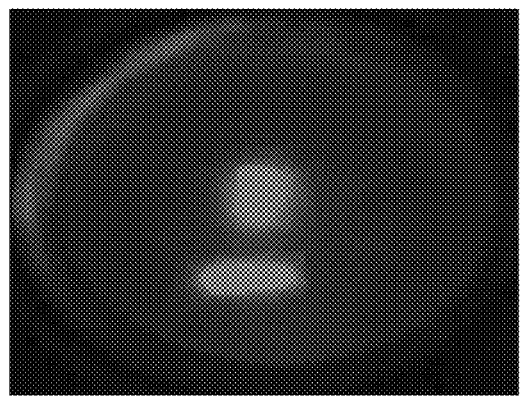

Figure 15
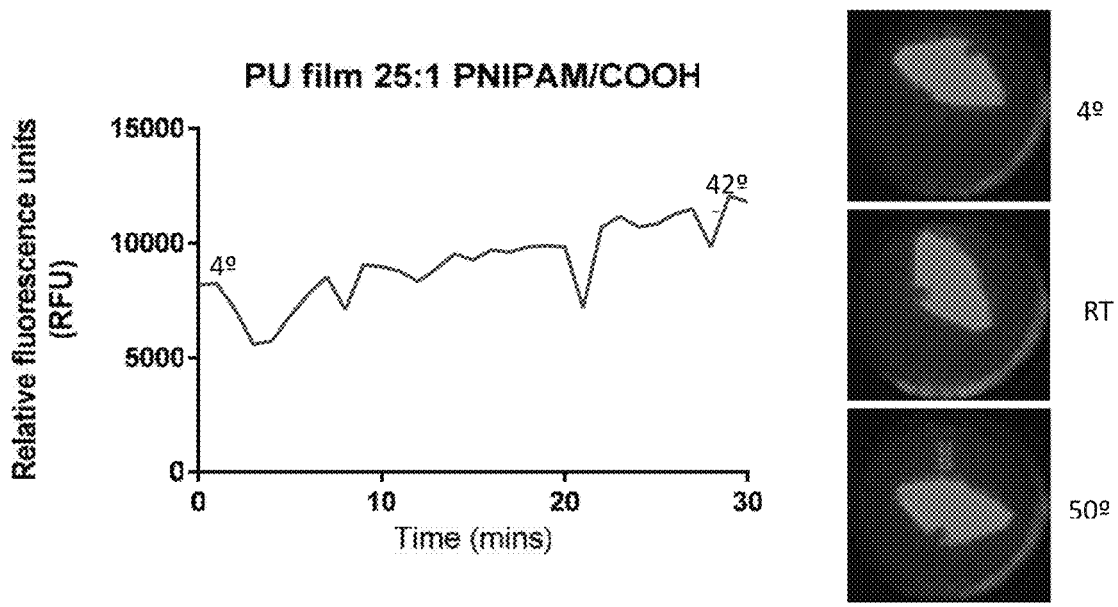
Figure 16 Selective Binding of bacteria (by gram type) by polymer in PU
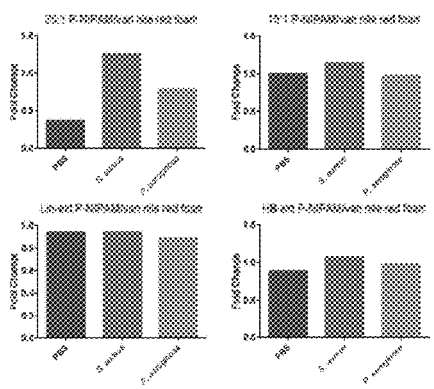

Figure 17 Bacterial Inhibition S. aureus (left: vancomycin; right : 25:1 P-NIPAM/van NR polymer)
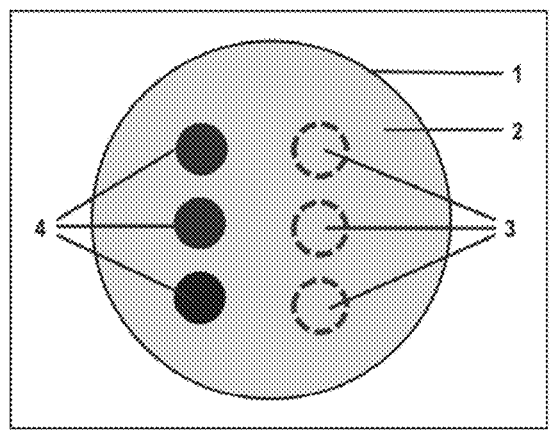
Figure 18 Bacterial recovery after binding
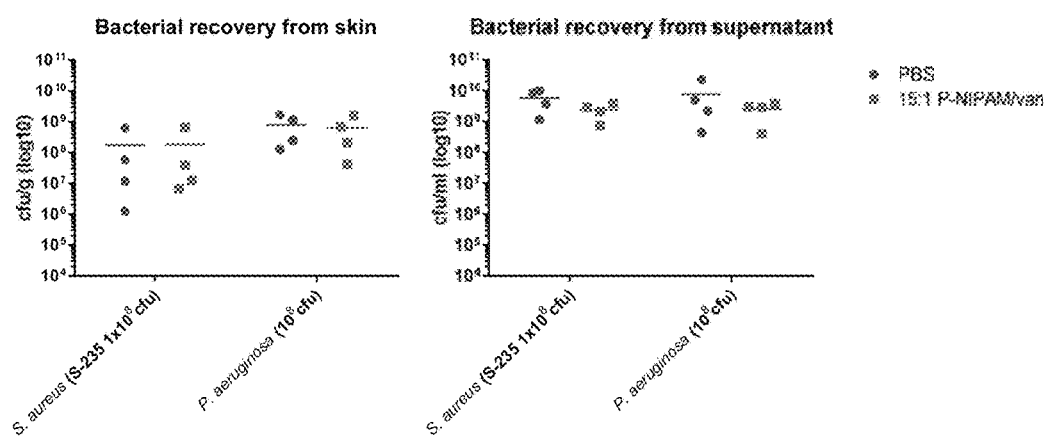

Figure 19
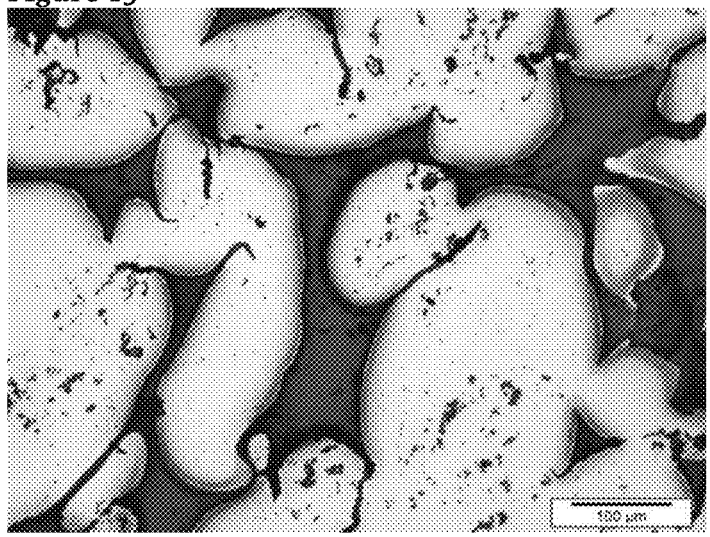
Figure 20 control foam with staph (100x)   Figure 21 Vancomycin foam in PBS (100x)
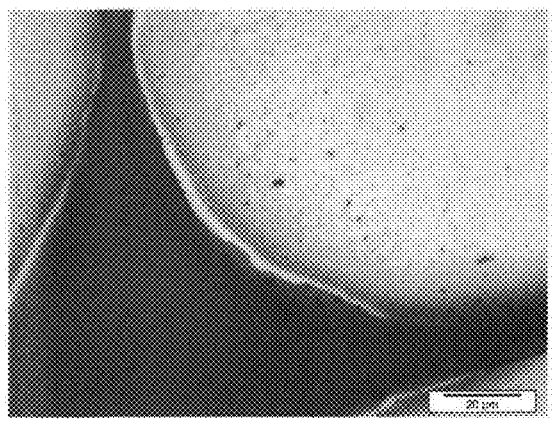 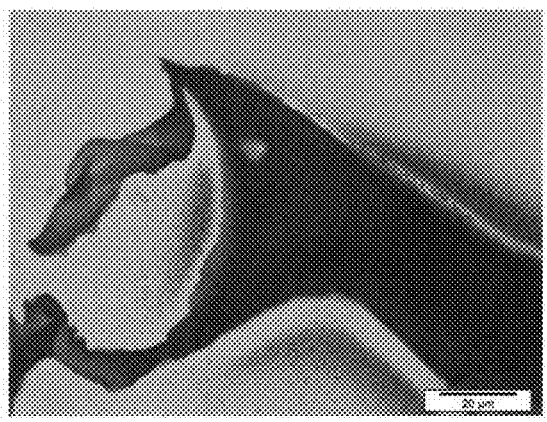
Figure 22   Vancomycin foam in PSA (100x) Figure 23   Vancomycin foam staph (100x)
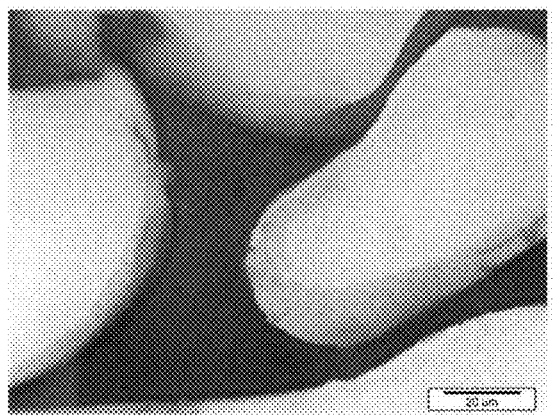 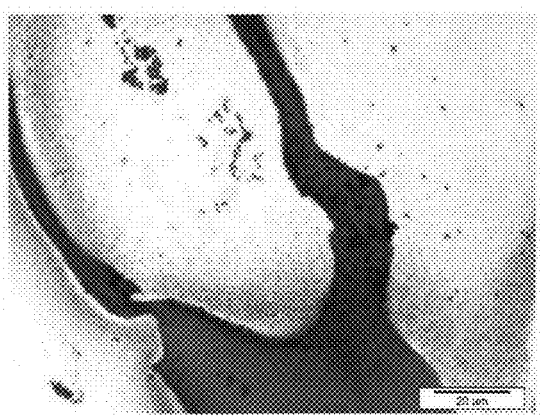

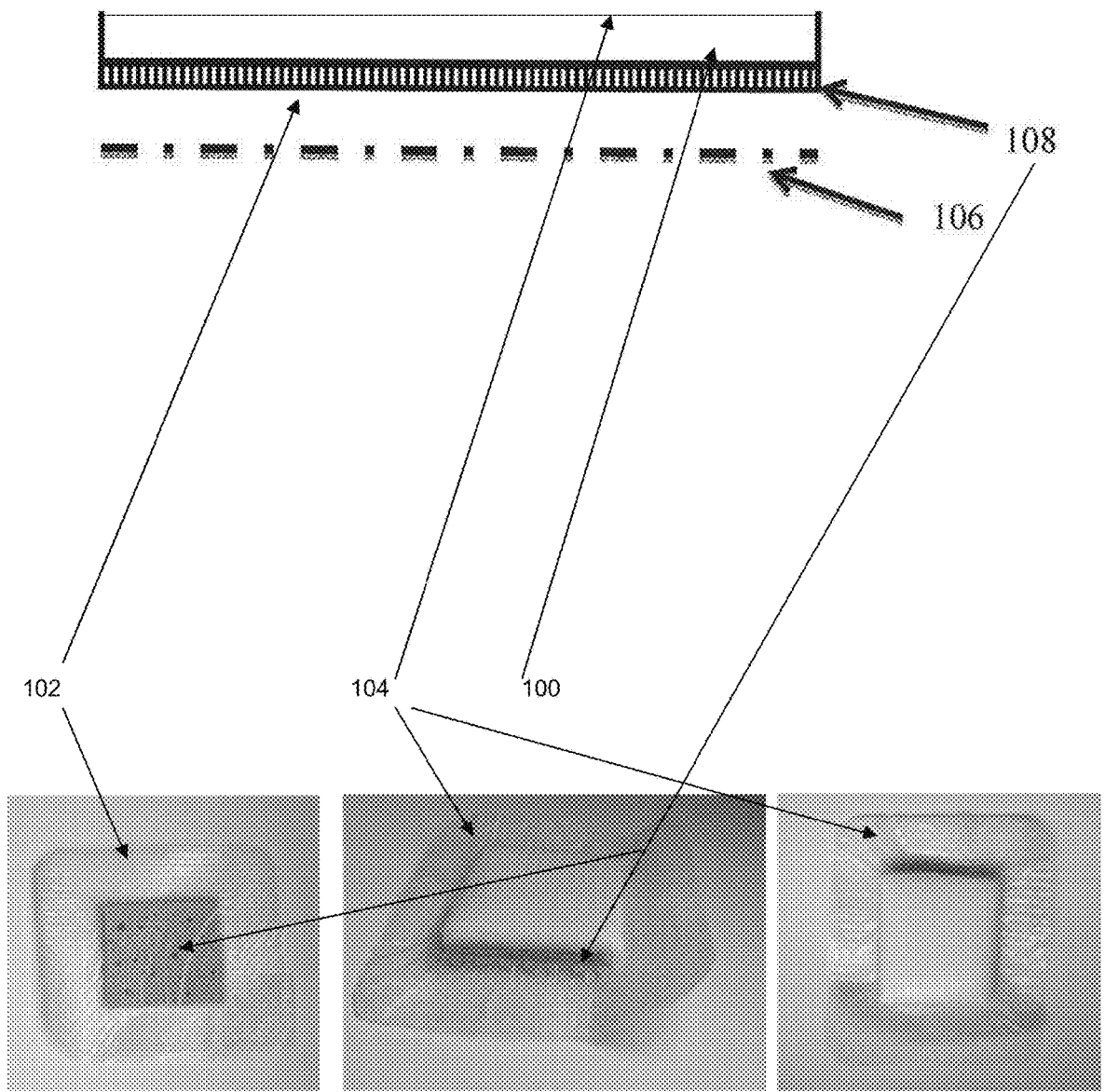

POLYMER MATERIALS

CROSS-REFERENCES TO RELATED APPLICATIONS

This application is a national stage application of International Patent Application No. PCT/EP2015/065234, filed on Jul. 3, 2015, titled "IMPROVEMENTS IN AND RELATING TO POLYMER MATERIALS," which claims priority to GB Patent Application No. GB1412427.5, filed Jul. 10, 2014, titled "IMPROVEMENTS IN AND RELATING TO POLYMER MATERIALS-I"; GB Patent Application No. GB 1412332.7, filed Jul. 10, 2014, titled "IMPROVEMENTS IN AND RELATING TO POLYMER MATERIALS-II"; GB Patent Application No. GB1412345.9, filed Jul. 10, 2014, titled "IMPROVEMENTS IN AND RELATING TO DEVICES"; GB Patent Application No. GB1506453.8, filed Apr. 16, 2015, titled "IMPROVEMENTS IN AND RELATING TO POLYMER MATERIALS—I"; GB Patent Application No. GB1506463.7, filed Apr. 16, 2015, titled "IMPROVEMENTS IN AND RELATING TO POLYMER MATERIALS—II"; and GB Patent Application No. GB1506451.2, filed Apr. 16, 2015, titled "IMPROVEMENTS IN AND RELATING TO DEVICES."

FIELD OF INVENTION

The present invention relates to polyurethane materials comprising immobilised hydrophilic polymer, such as stimulus responsive polyurethane materials for the detection or sensing of chemical or biological species or stimulus, devices comprising the same and to processes for their preparation and their use for example in medical care, dental care, sanitation, point of use sterilisation, hygiene, personal care or packaging.

More particularly the invention relates to such materials in form including foam, film, membrane, gel, mesh, fiber and the like, for the detection or sensing of chemical or biological species or stimulus such as bacteria, acid and base groups, pH and the like, to their devices, processes and use, and most particularly for the detection or sensing and/or binding of bacteria or detection or sensing of pH in wound management, sanitation applications and the like most particularly in woundcare, including care of moderately and highly exuding chronic and acute wounds, in sterilisation, hygiene or sanitation including air conditioning, water sanitation and the like.

BACKGROUND

Stimulus responsive polymers undergo a response event which drives the polymer through a phase change within a particular temperature range: the coil-to globule transition ($T_{c-g}$). The phase change may be observed directly or may be detected as a change in hydrophilicity or hydrophobicity of the polymer. The lower critical transition temperature (LCST) marks the transition temperature.

WO2010/094976 (Rimmer et al) discloses hyper branched, herein referred as highly branched, hydrophilic thermoresponsive polymers with bacteria binding functionality which can be used to remove infective bacteria from media such as wounds and biofluids. Thermoresponsive polymers belong to the general class of stimulus responsive polymers. These thermoresponsive polymers undergo a binding event on binding bacteria which drives the polymer through the $T_{c-g}$.

We have now found that adding these highly branched hydrophilic polymers to otherwise non-active polymeric materials and surfaces is an attractive proposition for conferring bacteria-binding functionality on such materials. However, in many instances simply mixing the functional polymer and non-active polymer material to produce blends produces material that is subject to leaching of the highly branched hydrophilic polymer. This occurs because the highly branched hydrophilic polymer is water-soluble and can generally be extracted into an aqueous phase, precluding application from solution or use in a medical application because of the aqueous environment. Therefore, in order to add such highly branched hydrophilic polymer to structural material used in medical devices it is necessary to prevent it from being leached.

There is therefore a need for a polymeric material comprising non-leachable bacteria binding polymer.

We therefore provide herein a polyurethane material for the detection or sensing of species or stimulus comprising a polyurethane network comprising immobilised therein, or modified by the immobilisation therein of,
a hydrophilic polymer comprising a ligand or moiety for the detection or sensing of species or stimulus by means of fluid contact therewith and comprising immobilised indicator for indicating detection or sensing
wherein species or stimulus is selected from chemical or biological species or stimulus.

Species are preferably selected from acid and base groups and microbes, preferably bacteria, yeast, fungus, and combinations thereof. Stimulus is suitably selected from temperature, pH, ionic strength, hydrophilicity, polarity and species-response.

Detection or sensing is suitably by means of intimate contact with species or stimulus or their environment. The material is preferably for sensing or detecting species or stimulus by means of intimate contact therewith. Immobilised ligand or moiety is bound to the hydrophilic polymer in manner that it remains bound in a fluid environment Polyurethanes/ureas may be formed by polymerisation of isocyanates and alcohols and/or water. Polyurethane networks such as chain extended or crosslinked polyurethanes may be formed by polymerisation of multi-functional alcohols with diisocyanates. We have now surprisingly found that highly branched hydrophilic bacteria-binding polymer may be immobilised in polyurethanes by mixing in during polyurethane polymerisation, more particularly during or prior to network formation such as during or prior to a chain extending step or a crosslinking step or during a step growth polymerisation step. A polyurethane network appears to grow in the presence of the highly branched hydrophilic polymer. The highly branched hydrophilic polymer appears to become entwined within, and penetrate, the network whereby it is unable to diffuse out of the polyurethane network.

In an extension of this work we have also discovered that corresponding linear or moderately branched hydrophilic polymers and block copolymers thereof may be immobilised by mixing in in similar manner. A polyurethane network appears to grow in the presence of any such hydrophilic polymer. The hydrophilic polymer appears to become entangled within the network whereby it is unable to diffuse out of the polyurethane network.

Preferably ligand or moiety and indicator are immobilised by means of network formation in the presence of hydrophilic polymer or part thereof or an amount thereof in fluid phase, preferably rendered in fluid phase by means of dissolution, solvation or the like.

A polyurethane material may be a stimulus-responsive polyurethane material comprising a polyurethane network modified by the immobilisation therein of a stimulus-responsive hydrophilic polymer.

An indicator such as the fluorescence dye nile red acrylate, covalently attached to the hydrophilic polymer chain backbone, allows for direct fluorescence interrogation of the hydrophobicity of the polymer coil and change in hydrophobicity on undergoing a stimulus response.

Alternatively or additionally a polyurethane material may be a species or stimulus indicating polyurethane material comprising a polyurethane network modified by the immobilisation therein of a hydrophilic polymer comprising an indicator for detection or sensing of species or stimulus. An indicator such as the fluorescence dye nile red acrylate, covalently attached to the hydrophilic polymer chain backbone, allows for direct fluorescence interrogation of the hydrophobicity of the hydrophilic polymer and change in hydrophobicity on detecting or sensing a species or stimulus.

Alternatively or additionally a polyurethane material may comprise a polyurethane network modified by the immobilisation therein of a linear hydrophilic polymer.

Preferably hydrophilic polymer is species-indicating or stimulus indicating hydrophilic polymer.

The polyurethane material may additionally be for monitoring species or stimulus as hereinbefore defined. Polyurethane material for monitoring provides for continuous or periodic sensing or detecting.

The polyurethane material may additionally be for assessing species or stimulus as hereinbefore defined. Polyurethane material for assessing provides for quantitation or qualification of sensing or detecting.

Preferably hydrophilic polymer comprises a ligand or moiety for sensing and/or detection of species or stimulus as hereinbefore defined. Preferably hydrophilic polymer comprises an indicator for indicating detection or sensing.

Preferably the material, and more preferably the hydrophilic polymer immobilised therein, comprises functionality for the detection and/or sensing, and/or binding of species which induce a stimulus response and/or comprises an indicator for a stimulus response. Preferably functionality comprises a ligand or moiety as hereinbefore defined.

The hydrophilic polymer may be highly branched or linear or a part or moiety thereof may be highly branched and a part or moiety thereof may be branched or linear. A highly branched or linear polymer may incorporate a part or moiety which is moderately branched. Such part highly branched part linear hydrophilic polymers are referred herein as extended polymers. Extended hydrophilic polymers are obtained with a first polyurethane reaction step conducted in the presence of a first hydrophilic polymer, the reaction extended with use of a second polyurethane reaction step conducted in the presence of a second hydrophilic polymer.

Highly branched polymer is also termed hyper branched in the art, reference herein to highly branched polymer is to be taken as referring also to such hyper branched polymer.

Reference herein to hydrophilic polymer is to include highly branched hydrophilic polymer, moderately branched hydrophilic polymer, linear hydrophilic polymer or block copolymers thereof herein termed extended hydrophilic polymer unless indicated as only one or several thereof or unless the sense dictates only one or several thereof.

In a further aspect there is provided a novel hydrophilic polymer comprising ligand or species as herein defined comprising at least one block copolymer of a highly branched hydrophilic polymer and a linear hydrophilic polymer as herein defined. Preferably the block copolymer comprises a core block and an outer or peripheral block or blocks. Preferably the block copolymer is characterised by its preparation wherein the core is prepared by the process for preparing one of highly branched and linear hydrophilic polymer and the process terminated and subsequently extended or recommenced following the process for preparing the other of highly branched and linear hydrophilic polymer. The polyurethane material may comprise one hydrophilic polymer or a plurality or blend thereof.

The LCST of the herein defined hydrophilic block polymers is dependent on the block architecture, in particular the architecture of the peripheral block.

Accordingly polyurethane material comprising a plurality or blend of hydrophilic block copolymers is characterised by multiple LCST. Preferably LCST fall in a range with the branched-branched polymers having a much lower LCST than the branched-linear equivalents. The polyurethane material is useful in detecting or sensing and quantifying species or stimulus.

In a further advantage polyurethane material comprising hydrophilic block copolymer providing a distribution of LCST provides for quantitative assessment of species or stimulus, wherein level of detected or sensed response is proportional to the amount of species or degree of proliferation thereof, or the degree of stimulus present.

Further features of the material are defined hereinbelow.

In a particular advantage the material comprises ligand or moiety, in particular comprises bacteria-binding or bacteria detecting ligand or moiety or functionality added to otherwise non-antibiotically active polymeric material. Such material is adapted for enabling in situ identification of bacteria with a non-antibiotically active material.

Without being limited to this theory we believe that the hydrophilic polymer retains the ability to bind bacteria, in addition to detecting or sensing.

Preferably ligand comprises antibiotic or a derivative thereof modified or immobilised or both in manner to be devoid of antibiotic activity or devoid of an ability to reorganise the outer membrane of bacteria, preferably to retain the capacity to sense or detect bacteria.

Suitably the material comprises non-leachable bacteria detecting or sensing and/or binding ligand or moiety or non-leachable bacteria detecting function, more particularly comprises non-leachable bacteria detecting or sensing hydrophilic polymer.

Suitably the material comprises polyurethane material as structural material having hydrophilic polymer comprising bacteria binding or bacteria detecting or sensing ligand or moiety or functionality immobilised within the structural material in manner to prevent the hydrophilic polymer, and more particularly thereby the bacteria detecting or sensing or binding ligand or moiety or functionality or function comprised thereby, from being leached.

Material for sensing and/or assessing and/or detecting microbes such as bacteria, as hereinbefore defined, is not classified as antibiotic material. Accordingly such material may be applied to an environment or a locus such as a wound site without the need for a prescription or other authority to medicate, in particular without the need for a prescription or other authority to apply antibiotic medication.

Preferably therefore such material is not intentionally antibiotic. Preferably the material, hydrophilic polymer and bacteria detecting or sensing ligand or moiety or functionality are configured to interact with live microbes such as bacteria in order to sense, assess or detect the presence thereof, however microbes such as bacteria remain live in contact with the material. Preferably microbes such as bacteria are substantially unchanged by interaction with the material, at least in terms of antibiotic resistance. Without being limited to this theory it is thought that microbes such as bacteria are not disrupted by interaction with the material, at least to an extent that might induce antibiotic resistance, or are not violated or entered as a result of contact with the material, at least to an extent that might induce antibiotic resistance. Preferably the material is not configured to release microbicide such as bactericide which might permanently interact with microbes or bacteria.

Polyurethane material is provided as structural material such as a sheet or layer. Providing as a sheet or layer ensures that polyurethane material is not washed away by water or aqueous media or physiological fluid such as wound fluid. Polyurethane material may thereby be positioned in a locus and retained in position in the locus.

Hydrophilic polymer is immobilised within the polyurethane polymer network as hereinbefore defined. Suitably indicator is immobilised on the hydrophilic polymer, preferably is covalently bound thereto.

Suitably ligand or moiety is immobilised on the hydrophilic polymer, preferably is covalently bound thereto. Reference herein to immobilisation or to a hydrophilic polymer. ligand or indicator being immobilised within or by a component such as the polyurethane polymer network or the hydrophilic polymer is to its presence within or on that component and remaining within or on that component throughout the intended use or lifetime of the material.

Preferably hydrophilic polymer and thereby indicator is distributed throughout the polyurethane material. Hydrophilic polymer and thereby indicator are thus characterised by location within the polyurethane material. Hydrophilic polymer and/or indicator may be associated with or may provide location information. Location information may for example be in the form of a material map. For example indicator may provide location information for indication or change of indication such as a material map of indication or change of indication. Suitably indicator is adapted to detect or sense species or ligand in the direct vicinity thereof.

Preferably hydrophilic polymer, ligand or moiety and/or indicator remain immobilised in the presence of water, aqueous media or physiological fluid and the like at ambient temperature such as in the range 0-45 C, most particularly under physiological conditions. Immobilised hydrophilic polymer, ligand, moiety and/or indicator are thus retained within or on the material. Hydrophilic polymer. Ligand, moiety and/or indicator are thus able to sense, detect or indicate bacteria present or pH at the polyurethane material. Immobilised hydrophilic polymer, ligand, moiety and/or indicator may be retained at one or a plurality of zones within or on the polyurethane material. Hydrophilic polymer, ligand, moiety and/or indicator are thus able to sense, detect or indicate bacteria or pH at the zone.

In a particular advantage the polyurethane material is obtained in a simple manner that involves only blending of hydrophilic polymer with polyurethane reaction components or polymerisation components.

Preferably therefore the hydrophilic polymer is immobilised within the network by introduction during the polymerisation reaction, which may be during formation of prepolymer or step growth of the polyurethane material whereby the hydrophilic polymer is present during the growth of the network, or during chain extension or crosslinking thereof.

BRIEF DESCRIPTION OF THE INVENTION

Preferably a polyurethane material such as a stimulus responsive polyurethane material comprises a polyurethane network such as a chain extended or crosslinked polyurethane network having a hydrophilic polymer for example such as a highly branched and/or moderately branched and/or linear hydrophilic polymer immobilised within the polyurethane network
wherein the hydrophilic polymer is responsive to one or more stimuli or change in one or more stimuli selected from temperature, pH, ionic strength, hydrophilicity, polarity and interaction, sensing or binding of species which confer such change.

Response to stimulus selected from temperature, pH and ionic strength, hydrophilic factors and polar factors may be induced or modified by one or more species or by an environment exhibiting any such stimulus and in particular exhibiting polar or hydrophilic stimulus or by species conferring such stimulus or environment on or in proximity of the material.

The present invention may on the other hand be defined in its broadest aspect as providing polyurethane material such as stimulus-responsive polyurethane material comprising a polyurethane network for example such as a chain extended or crosslinked polyurethane network having a highly branched and/or moderately branched and/or linear hydrophilic polymer immobilised within the polyurethane network wherein the hydrophilic polymer is selected from poly acrylamide, polyalkyl acrylamide, polyallyl acrylamide, polyacrylic acid, polymethacrylic acid,
water soluble polymers exhibiting $T_{c-g}$ in a useful physiological temperature range or temperature range prevailing in a locus or environment as hereinbefore defined and copolymers thereof.

Immobilised hydrophilic polymer is conveniently introduced in the manner of a semi interpenetrating network (s-IPN) or entangled network with the polyurethane network. Immobilised highly branched hydrophilic polymer such as for example stimulus-responsive polymer may be present in the form of a semi interpenetrating network (s-IPN) within the polyurethane network. Immobilised hydrophilic polymer which is moderately branched or linear or a combination thereof with highly branched polymer may be present in the form of an entangled network with the polyurethane network.

Alternatively or additionally immobilised hydrophilic polymer may be subject to other bonding or polar or ionic attraction with the polyurethane network.

Immobilised hydrophilic polymer is that polymer remaining after generation of the polyurethane network, preferably after process work up, including subsequent processing steps such as isolation thereof from polymerisation medium and washing.

Effective immobilisation may conveniently be assessed for example by residual extraction in an aqueous solvent for the polymer.

In a particular advantage, immobilised hydrophilic polymer is retained within the polyurethane network under conditions including or selected from aqueous conditions, aqueous solvent conditions, such as physiological medium, and conditions for detection and/or binding of species including or selected from bacteria, acid or base conditions and the like.

The stimulus-responsive polyurethane material is in the form of an entrapped semi interpenetrating network (ES-IPN) of a chain extended or crosslinked polyurethane polymer penetrated by a highly branched hydrophilic polymer as hereinbefore defined. By this is meant that it follows the same synthesis route as that of an ES-IPN although we cannot be certain that it forms a true IPN structure. Significantly the stimulus-responsive polyurethane material is the product of polymerisation in the presence of the highly branched hydrophilic polymer. Suitably the stimulus-responsive polyurethane material is the product of polymerisation reaction in the presence of the highly branched hydrophilic polymer. Polymerisation reaction, which may be classed for example as step growth polymerisation, causes the polyurethane chains to grow about and through the highly branched hydrophilic polymer which thus becomes entwined and entrapped within the polyurethane network.

A fully or semi-interpenetrating network (F-IPN or S-IPN) is defined as a polymer comprising two or more crosslinked networks or comprising one or more crosslinked polymer networks and one or more polymers or macromolecules characterized by the two or more crosslinked networks interpenetrating each other or by the one or more network penetrating on a molecular scale the polymer or macromolecule. Such S-IPNs allow theoretical separation of network and polymer or macromolecule without breaking of bonds.

S-IPNs and F-IPNs are of great utility in many sectors because they can provide materials with properties and functionality of both components. However F-IPNs are difficult to manufacture because it is often necessary to find either concurrent polymerisation processes that do not interfere with each other or to swell a preformed network with another monomer and then polymerise this polymer/monomer blend. The concurrent polymerisation route is only applicable to certain combinations of materials and the swelling approach can produce distortions of premolded devices. On the other hand S-IPNS that can be more easily manufactured by mixing in a macromolecule during the polymerisation and crosslinking of the network polymer, are often used in contact with fluids that swell the crosslinked component and dissolve the linear component and are not useful because they are separable both in theory and in practice, as the linear component is easily extracted or is capable of leaching from the crosslinked component.

The present invention relates to the improvement of S-IPNs in the form of the ES-IPN as hereinbefore defined wherein the highly branched hydrophilic polymer is entwined within and penetrated by the chain extended or crosslinked polyurethane polymer network and thereby entrapped therein. We have surprisingly found that the highly branched hydrophilic polymer as hereinbefore defined is separable from the penetrating network in theory only and not in practice and is not capable of leaching or of being extracted from the chain extended or crosslinked polyurethane polymer network. Without being limited to this theory the highly branched hydrophilic polymer is not capable of diffusing through the network because the branch points can not diffuse past the chains or crosslinks of the network. Alternatively or additionally some or all or part of the highly branched hydrophilic polymer forms bonds with the polyurethane, in the form of H-bonds, covalent bonds, grafts or other interactions. Bonds remain intact in the presence of aqueous solvent. Immobilisation of highly branched hydrophilic polymer may be the result of such bond formation or of entrapment by the penetrating network or both.

In the second embodiment the invention relates to the improvement of entangled networks as known in the art wherein a linear hydrophilic polymer is entangled by the chain extended or crosslinked polyurethane polymer network and thereby entrapped therein. We have surprisingly found that the linear hydrophilic polymer as hereinbefore defined is separable from the penetrating network in theory only and not in practice and is not capable of leaching or of being extracted from the polyurethane polymer network.

Without being limited to this theory the linear hydrophilic polymer is not capable of diffusing through the network because the polymer is entangled such that it can not diffuse out of the network. For example the polymer may be entangled or comprise internal steric factors or polar attractions such that it resembles a highly branched hydrophilic polymer and behaves in manner as hereinbefore defined for ES-IPNs.

We have surprisingly found that the hereinbefore and hereinbelow defined polyurethane material such as stimulus-responsive polyurethane material does not release the entrapped or entangled hydrophilic polymer. Upon exhaustive washing in solvents effective for the copolymer, such as aqueous ethanol, ethanol, dichloromethane or acetone, the copolymer remains held in the polyurethane network, despite polarity, lipid effects, swelling or safety of the polyurethane network in said solvents. The copolymer is therefore held in manner such that it is resistant to removal by swelling of the surrounding polymer network, by solvent extraction or by solvation effects.

We have shown that the herein defined hydrophilic polymer is immobilized in the polyurethane material with use of a range of solvents with differing degrees of polarity solvating power to attempt to remove the hydrophilic polymer from the polyurethane network. Solvents included:
water containing ethanol (5%),
dichloromethane (DCM),
acetone
ethanol and
DMSO.

DCM is the least polar and DMSO the most polar.

Solvents were selected from a consideration of the increasing solubility of the hydrophilic polymer with increasing solvent polarity. Solvents were further selected from a consideration of the ability of the solvent to swell the polyurethane material.

DMSO presents the solvent most likely to remove the material in view both of polarity and swelling of polyurethane material.

Polyurethane material was prepared for solvent extraction by work up to remove residual or low MW hydrophilic polymer entrained within the network.

Immobilised hydrophilic polymer was not leached from the polyurethane by any solvent.

Preferably therefore highly branched hydrophilic polymer is functionalised by attachment to said polymer of ligand possessing the facility to detect or sense microbes or pH, for example to detect or sense species or stimulus including microbes such as bacteria and acid or base groups and pH. Preferably hydrophilic polymer is functionalised by covalently bound bacteria sensing or pH sensing ligand or moieties.

More preferably polymer is highly functionalised by attachment of one or more ligands or moieties at a plurality or multitude of branches, preferably at the termini of said branches or at a plurality of positions along the hydrophilic polymer backbone and at the ends thereof. Preferred highly branched polymer adopts a fully solvated open coil structure below the LCST whereby ligands are highly exposed and available to take part in species binding or aggregation events. Preferably response to a change in stimulus as hereinbefore defined is induced by a species binding or aggregation event involving said ligand(s).

Herein microbial or microbes include bacterial or bacteria, yeast, fungal, fungus or fungi or combinations thereof.

Reference hereinabove and hereinbelow to bacteria includes reference to microbes unless otherwise specifically indicated or unless the sense dictates otherwise.

The material may be rigid or conformable. Preferably the material is conformable.

A material as hereinbefore defined is preferably configured for detecting or sensing species or stimulus present in or comprised in an environment preferably in an environment comprising or containing or consisting of or associated with fluid, in particular aqueous fluid including aqueous liquids and vapours such as moisture and physiological fluids. The material is preferably configured to be in fluid communication with such environment. Preferably such environment is a moist environment such as an exuding or humid environment, for example an exuding or humid wound environment or an associated environment such as a wound fluid reservoir or conduit. A material as hereinbefore defined may be activated by fluid contact In a further advantage the polyurethane material is for monitoring of species or stimulus response. This enables for the first time the real time in situ monitoring of species or stimulus or change in species present or in stimulus in a vicinity of or locus of polyurethane material.

In a particular advantage the polyurethane material as hereinbefore defined comprises an indicator which indicates the detection or sensing of species or stimulus or stimulus response by means of an optical change such as a change in colour, more particularly as a change in fluorescence, or intensity, quantity, magnitude or signal thereof such as wavelength, or a molecular or phase change, more preferably a change in adsorption or emission spectra in the UV, visible or Infra red regions of the electromagnetic spectrum, most preferably as a change in fluorescence or fluorescence intensity.

Indication may be by means of stimulus response and/or of indicator comprised within the material. Preferably hydrophilic polymer or a moiety thereof is a copolymer of a hydrophilic monomer and an indicating monomer.

Preferably the hydrophilic polymer is functionalised by the attachment to said polymer of indicator in chain or at branch termini. Indicator may for example comprise one or more dyes, imaging agents, indicating monomers or markers which undergo a detectable change, for example on interaction or binding with bacteria.

Wounds can become infected and there is no quick and easy way to determine if the bacteria present are Gram negative or Gram positive and thus to determine an appropriate treatment regime.

In the past the identification of bacteria in a locus such as a wound has necessitated invasive sampling such as by tissue biopsy, withdrawing a swab or wound fluid sample for testing, investigating pH by probe and the like.

The field of wound care management has long understood that the pH of a wound can be an indication of wound healing status and can indicate when further action may be necessary to aid wound healing. The pH can affect many factors including oxygen release, angiogenesis, protease activity and bacterial toxicity. Acute and chronic wounds with an elevated alkaline pH have been shown to have lower rates of healing than wounds in which the pH is closer to neutral. For example, if a chronic wound has a pH of between 6 to 7.5 this indicates that wound healing is progressing well. In comparison, if the pH is between 7.5 and 8, this indicates that the wound should be monitored and a pH of above 8 indicates that clinical intervention is required. It is therefore important to be able to monitor wound pH in order to be able to assess wound healing and intervene, if necessary.

We have now surprisingly found that the hereinbefore defined polyurethane material enables the provision of a material or device such as a dressing or the like incorporating ligand and indicator for real time detecting and/or sensing and/or monitoring species such as bacteria, acid and base groups and stimulus as hereinbefore defined, and indication thereof in situ. For example the binding of bacteria may be evidenced by visual inspection or scan in situ of the material such as a dressing cover layer or wound contact layer, for change in indication or appearance thereof.

Moreover polyurethane material enables visualisation of bacteria, for example at a locus such as a wound.

We have been able to introduce hydrophilic polymer within a polyurethane network, whereby it is immobilised therein and is not leached.

We have shown the following:

incorporation of highly branched, linear or extended PNIPAM with carboxylic acid or succinimide end groups into a polyurethane foam and extraction studies to show that PNIPAM can be immobilised and cannot be removed.

incorporation of highly branched, linear or extended PNIPAM with bacteria binding end groups into a polyurethane foam and extraction studies to show that the PNIPAM can be immobilised and cannot be removed.

incorporation of highly branched, linear or extended PNIPAM with carboxylic acid or bacteria binding end groups and with nile red labels along the polymer chain into a polyurethane foam or film and extraction studies to show that the PNIPAM can be immobilised and cannot be removed.

We have shown selective bacterial binding by type indicating whether bacteria is Gram positive or Gram negative.

Reference hereinbelow to hydrophilic polymer as highly branched or linear may be read interchangeably unless the sense dictates otherwise.

DESCRIPTION OF THE FIGURES

FIGS. 5 and 6 illustrate stimulus response of samples;

FIG. 7 illustrates material herein;

FIGS. 8 and 9 illustrate retention and hydrophilic polymer loading of material herein;

FIG. 10 illustrates distribution of hydrophilic polymer throughout histological section of material herein;

FIGS. 11-15 illustrate fluorescent activity of material herein;

FIG. 16 illustrates selective binding of bacteria by material herein;

FIGS. 17 and 18 illustrate material herein as bacterially non-inhibiting;

FIG. 19 illustrates Gram stain of P-NIPAM/van nile red polyurethane foam;

FIGS. 20 to 23 illustrate Gram stains of material herein showing type specific binding and indication of bacteria.

FIGS. 24 and 25A-25C illustrate a dressing herein.

DETAILED DESCRIPTION

Stimulus-Responsive Polyurethane Material

Figure 1:
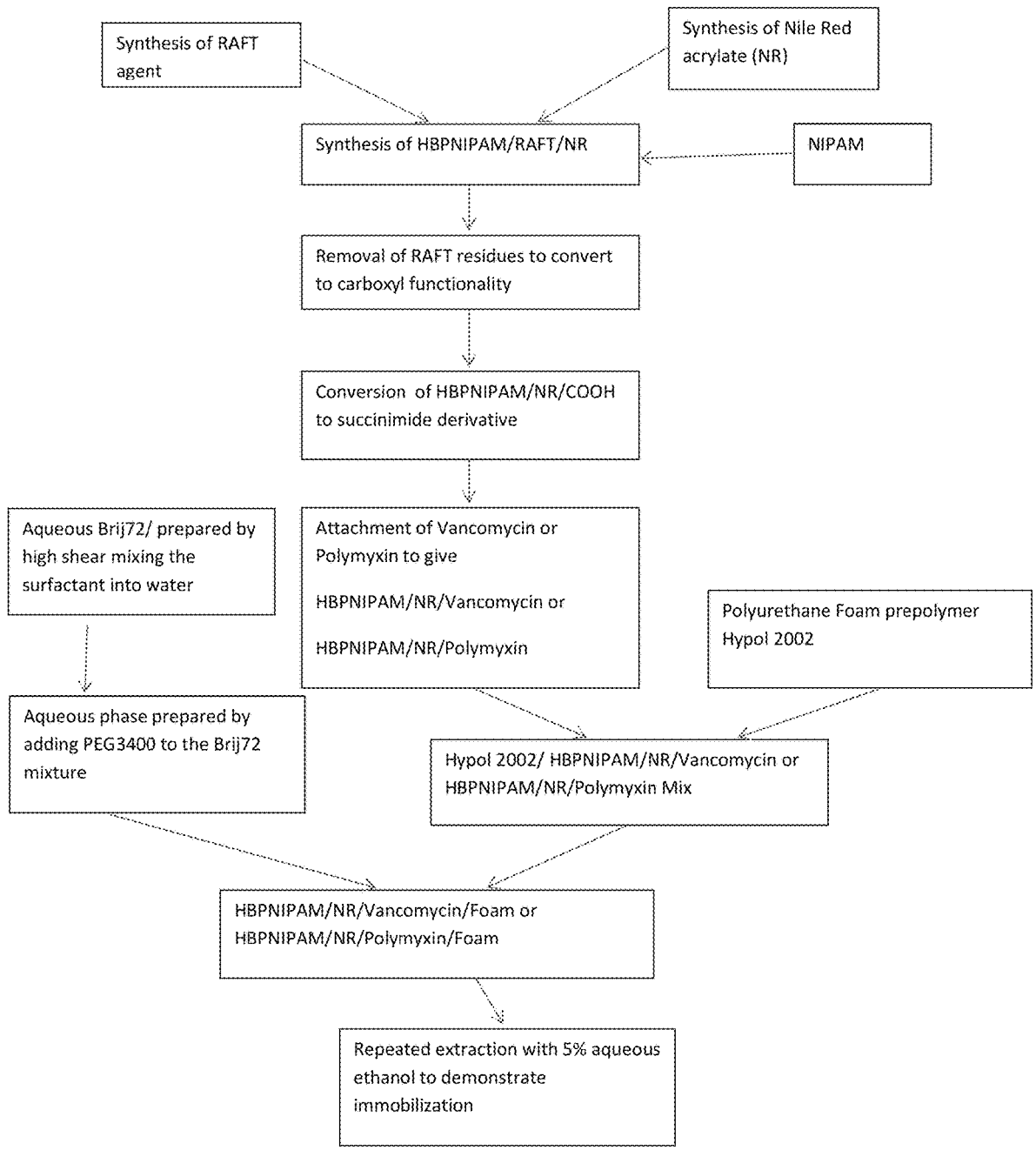
FIGS. 1 and 2 illustrate schemes for the preparation of herein defined polyurethane material.

Highly branched hydrophilic polymer as hereinbefore defined such as poly(N-isopropylacrylamide) (PNIPAM or PIPAAm) preferably dissolve in aqueous media below a critical temperature, herein referred to as the lower critical solution temperature (LCST). As the temperature is raised above the LCST, the polymer forms primary particles which aggregate and then undergo sedimentation in the reaction vessel to form a solid mass. Such polymers having a temperature dependent solubility are known as thermo-responsive polymers, and generically as stimulus responsive polymers.

The macroscopic changes that can occur at critical values of pH, temperature or ionic strength with such polymers come about because the polymer changes from an open (solvated) coil to a collapsed state known as a globule. Any aqueous polymer solution will respond in this way to changes in pH, temperature or ionic strength but, for many systems, the critical points occur at temperatures that are above 100 C or below 0 C.

Functionalised stimulus responsive polymers are disclosed in WO2010/094976 hereinabove in the form of hyper branched, otherwise termed highly branched, hydrophilic thermoresponsive polymers with bacteria binding functionality. These functional polymers respond to bacterial binding by passing through a desolvation driven transition in which the polymer passes from a fully solvated open coil to a desolvated globular structure (Tc-g). This desolvation of highly solvated ligands produces a large perturbation in the overall solvency of the polymer and this perturbation can produce significant decreases in its lower critical solution temperature (LCST) to the extent that polymer collapse to globule can occur at body temperature.

Such functionalisation of highly branched stimulus responsive polymers to bind bacteria can usefully induce or modify stimulus response and LCST. For example functionalisation to confer an ability to bond or interact with species such as bacteria or with polar or hydrophilic environments drives the polymer into its collapsed state at a temperature below its LCST, its LCST is typically above 60 C. Consequently there is no need for precise control of temperature in the handling of this polymer because it will not spontaneously change conformation at room temperature or body temperature, but will only collapse at this temperature when bacteria bind to it.

Preferably therefore the highly branched hydrophilic polymer is functionalised by attachment to said polymer of ligand possessing the facility to interact with species in manner to induce or modify stimulus response. More preferably the response to stimulus is a change in LCST, such as a reduction in LCST. This can be harnessed to advantage by reduction in LCST to within an intended temperature range of use, for example within the temperature range of the environment within which the material is to be responsive. In the case of medical applications, the LCST may be influenced by modification to lie within the range from room temperature to physiological body temperature.

Polyurethane Material

Polyurethane material may be in any form suited for the intended purpose. Preferably polyurethane material is in the form of a foam, film, perforated film, membrane, water impermeable membrane providing moisture vapour transmission (MVT), adhesive layer or coating, sheet, block, non-woven or woven fabric, fibers and the like and combinations thereof.

Polyurethane material in a form as hereinbefore defined may be foamed, unfoamed or xerogel.

A foam is preferably open cell as known in the art. We have found that a polyurethane foam formation is not disrupted by the presence of the hydrophilic polymer.

A xerogel is a solid formed from a gel by drying with unhindered shrinkage. Xerogels usually retain high porosity (15-50%) and enormous surface area (150-900 m$^2$/g), along with very small pore size (1-10 nm).

Xerogels are well suited to the immobilisation of hydrophilic polymer as hereinbefore defined in gel form. An adhesive layer or coating may be applied to a device or part thereof as a gel, more preferably a xerogel, as known in the art.

Preferably polyurethane material possesses the facility to conform to or be deformed or conformed to fit or cover a locus such as a wound surface. Conformable material possesses the advantages of facilitating mapping of species across a surface for example mapping bacteria or pH profiles across a locus, in particular a wound. This has clear benefits over detecting bacteria or pH at isolated locations. Mapping is particularly advantageous as the pH or bacteria in a wound is often not uniform across the wound. Importantly it is surmised that all wounds contain sub critical levels of bacteria, however as the population increases it reaches a detrimental magnitude in the wound which is classified in order of severity as contaminated, colonised, critically colonised and ultimately as infection level. These levels are given the meaning known in the art. Advantages are also apparent in the use of the herein defined polyurethane materials in relation to systems from which bacteria can readily propagate and for which it is desired to rapidly identify the source or epicentre of detected bacteria or their population, such as in relation to wounds, air conditioning systems, water management systems and the like. Polyurethane material in the form of conformable cover material as hereinbefore defined confers the facility to detect the location of a bacterial population which is of detrimental magnitude.

Polyurethane Network

Preferably polyurethane network is the product of reaction of an isocyanate terminated monomer and a long chain diol and/or polyol.

Reaction generates the isocyanate terminated oligomeric prepolymer.

The polyurethane network is the result of chain extension or crosslinking said isocyanate terminated oligomeric prepolymer, with use of chain extending long chain diol and/or polyol or crosslinking agent which may be introduced simultaneously with or subsequent to the polymerisation reaction.

Isocyanate terminated monomer may be aromatic or aliphatic. Preferably aromatic isocyanate terminated monomer is selected from one or more of toluene diisocyanate (TDI), methylenediphenyl isocyanate (MDI), para phenylene diisocyanate (PPDI) and naphthalene diisocyanate (NDI).

Preferably aliphatic isocyanate terminated monomer is selected from one or more of hexamethylene diisocyanate and dicyclohexyl methyl diisocyanate (hydrogenated MDI) and the like.

Long chain diol or polyol is conveniently selected from one or more polyols or diols of polyester, polycaprolactone, polyether and polycarbonate, more preferably the polyols thereof. For example polyether long chain polyol is selected from polytetramethylene ether glycol (PTMEG), polyoxypropylene glycol (PPG) and polyoxyethylene glycol (PEG).

Isocyanate terminated monomer and long chain diol or polyol are conveniently provided in the form of an isocyanate terminated polyether prepolymer thereof for example as commercially available in the range of HYPOL polyurethane prepolymers (W R Grace & Co). HYPOL prepolymer includes prepolymer of aromatic isocyanates HYPOL polyurethane foams may be prepared by reacting the isocyanate terminated polyether prepolymer with water.

Non-foamed HYPOL polyurethane such as blocks, films, membranes or the like may be prepared by reacting the isocyanate terminated polyether prepolymer with diol or polyol.

Essentially non aqueous polyurethane such as xerogel may be prepared by reacting a prepolymer of a polyisocyanate and a polyol such as a glycol such as diethylene glycol or low molecular weight polyethylene glycol or polypropylene glycol (PEG or PPG). Such polyisocyanate may be an aliphatic polyisocyanate. Such polyisocyanate is commercially available for example as Desmodur N100.

Hydrophilic Polymer

Suitably the hydrophilic polymer is combined with the polyurethane components prior to casting into a mould or onto a surface. Polyurethane material may be cast into a mould or onto a surface to form a foamed or non foamed block or sheet, gel, membrane or film, or to form fibers or the like.

It is one benefit of the invention that hydrophilic polymer may be simply blended with the polyurethane components or ingredients during the reaction thereof and prior to chain extension or crosslinking, whereby it is immobilised within the polyurethane network. Hydrophilic polymer may be blended with one of the polyurethane components or ingredients prior to combining the respective components or ingredients. For example hydrophilic polymer may be combined with an isocyanate component or polyol component or both such as the HYPOL phase or the long chain diol and/or polyol phase in a polyurethane system.

Preferably the hydrophilic polymer is provided in fluid phase, preferably dissolved in solvent prior to combining with one or more polymerisation reaction components or dissolved or solvated in situ in one or more of the polymerisation reaction components. Hydrophilic polymer introduced in dissolved form is more readily able to form an interpenetrating or entangled network with the polyurethane polymer.

Hydrophilic polymer provides a hydrophilic environment. Polymer or indicator immobilised thereon, provides an indication or response on change of hydrophilic nature of environment, such as increase or decrease in hydrophilicity, or decease or increase in polarity. In particular in a material as hereinbefore defined, a decrease in hydrophilicity is initiated by a number of factors including presence of lipid membranes such as in microbial environments. Change in hydrophilicity may be local, i.e. may occur within or specific to zones of the hydrophilic polymer and thereby within or specific to zones of the polyurethane material.

Indicator is comprised in the hydrophilic polymer, preferably covalently bound thereto, more preferably as a copolymer as hereinbefore defined. Indicator is configured to provide indication and change of indication in relation to the directly proximal zone of the hydrophilic polymer or surface. In a particular advantage the material is thereby configured to provide indication relating to location of detected species or stimulus such as bacteria, acid or base groups or pH.

Hydrophilic polymer may be provided in the polyurethane material in any desired amount. Hydrophilic polymer may be present in an amount from a trace amount up to the maximum amount which the chain extension or crosslinking process tolerates. Preferably hydrophilic polymer is present in an amount greater than or equal to a trace amount, preferably in an amount of from 0.01 wt % up to 20 wt %, such as from 0.1 wt % up to 20 wt %. preferably from 1 wt % up to 20 wt % An economic consideration promotes operation in the lower end of the range for example from 0.01 wt % to from 4 wt %, balanced against performance consideration which promotes operation in an intermediate region or upper end of the range for example from 4-20 wt %, for example 4-15 wt %. In a particular advantage we have found that it is possible to achieve amounts of hydrophilic polymer in the range 6-20 wt %, for example 6-15 wt %.

Highly branched hydrophilic polymer or linear hydrophilic polymer is preferably selected from polyacrylamides, polyacrylic acids, such as poly acrylamide, polyalkyl acrylamide, polyallyl acrylamide, polyacrylic acid, polymethacrylic acid, and their copolymers, polymers of acidic monomers and polymers of cationic monomers. More preferably the highly branched hydrophilic polymer is selected from polyalkyl acrylamide wherein alkyl is ethyl, propyl or butyl such as poly(N-isopropyl acrylamide) (PNIPAM), polyacrylic acid, polymethacrylic acid, and copolymers thereof. Copolymers may be with other polymers or substrates. Copolymers may confer same or different responsivity.

Particularly envisaged for microbial detection is polyalkyl acrylamide, preferably wherein alkyl is ethyl, propyl or butyl more preferably poly(N-isopropyl acrylamide) (PNIPAM).

Particularly envisaged for pH detection are polyacrylic acid and polymethacrylic acid.

Highly branched hydrophilic polymer or linear hydrophilic polymer may be present in substantially uniform molecular weight or in a distribution of molecular weight. A distribution of molecular weight presents a distribution of total branching or chain length and thereby a distribution in total functionalization, i.e. ligand content. Advantageously such polymer provided in a distribution of molecular weight provides low, intermediate and high sensitivity response or indication thereof, for example of binding of species such as bacteria.

In a further advantage hydrophilic polymer present in a distribution of molecular weight provides for quantitative assessment of species or stimulus, wherein level of detected or sensed response is proportional to the amount of species or degree of proliferation thereof, or the degree of stimulus present.

Highly Branched Hydrophilic Polymer

Highly branched stimulus responsive polymer or highly branched hydrophilic polymer is also known in the art as hyper branched. The degree of branching may vary and may be expressed in a number of ways, for example as the number of branched sites divided by the total number of monomer sites.

It is perhaps more convenient to consider the polymer as comprising a plurality of repeat units and a plurality of branch points wherein the degree of branching is defined as the ratio of repeat units to branch points. Preferably the highly branched hydrophilic polymer as hereinbefore defined is characterised by a ratio of repeat units to branch points of less than 45:1, preferably less than 35:1, such as less than 30:1, and preferably less than 20:1. For example in the range 5-45:1, preferably 8-35:1, more preferably 10-30:1, most preferably 12-20:1. This corresponds to the ratio of monomer to polymerisation agent or branching agent. Preferably monomer:branching agent, for example RAFT agent, is in the range 5-45:1, preferably 8-35:1, more preferably 10-30:1, most preferably 12-20:1.

Sensing or Detecting Ligand or Moiety

Ligand or moiety is preferably covalently bound to the hydrophilic polymer.

Ligand or moiety may be covalently bound to attachment groups such as for example carboxylic acid or succinimide groups.

Preferably hydrophilic polymer is a copolymer with attachment monomer providing attachment groups.

Preferably linear hydrophilic polymer is a copolymer of the hereinbefore defined monomers with attachment monomer for example such as vinyl benzoic acid.

Preferably highly branched hydrophilic polymer is a copolymer of the hereinbefore defined monomers with attachment monomer for example such as RAFT monomer.

Alternatively ligand or moiety may comprise functional groups provided by the hydrophilic polymer, or provided by interchange of functional groups provided by the hydrophilic polymer. Ligand or moiety may for example comprise acidic or basic functional groups.

Ligand or moiety is preferably provided at the polymer chain termini including the ends of a plurality of the polymer branches or the ends of the polymer backbone, and optionally additionally at a plurality of sites along the polymer backbone. Ligand or moiety may be provided at substantially all of the polymer branches or backbone sites and termini or at a percentage thereof.

Ligand may be bound in any convenient ratio within the hydrophilic polymer, for example up to 35:1 ligand:hydrophilic polymer.

We have found that there is an optimum range of binding ratio at the lower end of which the hydrophilic polymer presents sufficient ligand to give a measurable response and at the upper end of which the ligand is oriented to be freely available to detect bacteria. Above this optimum range it is possible that access to ligands becomes obstructed and some ligand becomes unavailable for binding.

In an advantage, ligand present in high ratio as hereinbefore defined possesses the facility to gather or accumulate species such as bacteria by binding or interaction, in manner to create a species dominant environment in the proximity of the hydrophilic polymer. We believe that this further enhances the range of sensitivity of detection, sensing or binding, and the facility of the polymer material to provide low, intermediate and high sensitivity indication of detection, sensing and/or binding, for example of species such as bacteria.

Hydrophilic polymer may comprise a plurality of ligands selective for a plurality of species or stimulus. A plurality of ligands may be provided on the same polymer molecule. Alternatively an amount of hydrophilic polymer may comprise a ligand selective for one species or stimulus and an amount of hydrophilic polymer may comprise a further ligand selective for a further species or stimulus.

In the case of more than one ligand, hydrophilic polymer may provide more than one indicator. One indicator may be specific for indicating sensing or detecting or binding by one ligand and a further indicator may be specific for indicating, sensing or detecting a further ligand.

Orientation of ligand in relation to the copolymer is not insignificant. Hydrophilic polymer suitably comprises ligand disposed in pendant manner, for example at branch termini, along the backbone or at chain termini.

Microbe detecting ligand or moiety is most preferably immobilised to hydrophilic polymer comprising a polyalkyl acrylamide or copolymer thereof.

pH sensing or detecting function or moiety is most preferably present immobilised by hydrophilic polymer such as for example polyacrylic acid, polymethacrylic acid or copolymer thereof.

Ligand or moiety is suitably provided as groups pendant to the hydrophilic polymer, at linear or branch termini, along the backbone or both.

The pH Sensing Function pH detecting function, hereinabove and hereinbelow ligand or moiety, is suitably selected from one or more acid groups or base groups. Preferably pH detecting function or moiety is selected from one or more acid groups, for example comprises —COOH groups.

pH detecting function response bears charge or is uncharged at different pH. —COOH groups are charged at high pH or are uncharged at low pH. Change in pH from high to low pH at a locus causes coil to globule collapse.

pH detection or pH of stimulus response is dependent on the pH sensing functionality or moiety. Depending on the pH sensing functionality or moiety, the coil to globule collapse in a stimulus responsive polymer as hereinbefore defined occurs at a given pKa, for example where a pH sensing functionality or moiety is —COOH the collapse is in the region of pKa 5.

Accordingly in material as hereinbefore defined, stimulus response is responsive to detecting or sensing species or stimulus or change in species or stimulus such as presence of microbes or change in pH, and indicator is responsive to stimulus response. Preferably stimulus is change of polarity or hydrophilicity and stimulus response is change of hydrophilicity of hydrophilic polymer, more preferably in the form of coil to globule collapse.

Indicator as hereinbefore defined is configured to indicate the detection or sensing of species or stimulus or coil to globule collapse.

Microbe Detecting Ligand

Microbe detecting function is suitably selected from one or more ligands or moieties which detect or sense, and optionally interact with or bind microbe. Ligand may be specific to a microbe or microbes which it is desired to detect and/or monitor.

Preferably ligand or moiety is selected from one or more peptide antibiotics and their bacteria derivatives including glycopeptides and lipopeptides, non-peptide antibiotics and their derivatives, antibody fragments that detect, sense or bind to bacteria, peptide sequences such as small RNA and DNA sequences such as apatemers, and oligo- and monosaccharides that detect, sense or bind to bacteria and combinations thereof. Other examples of suitable bacteria binding ligands include any low molecular weight compounds that selectively detect, sense and optionally bind to any cell surface receptor on bacteria. Especially suitable ligands are bacteria sensing or detecting or binding peptides and combinations thereof and in particular antibiotic or non-antibiotic peptides and their derivatives.

A derivative includes a modification which is devoid of bactericidal activity, herein is antimicrobially inactive, preferably antibiotically inactive. A derivative may retain the capacity to detect and interact with bacteria, for example to reorganise the outer membrane of bacteria.

Bacteria detecting, sensing and/or binding ligand or moiety is suitably selected from one or more ligands for interacting with or binding Gram positive bacteria and/or one or more ligands for interacting with or binding Gram negative bacteria. Hydrophilic polymer may comprise one or more ligands selective for Gram positive bacteria and one or more ligands selective for Gram negative bacteria provided on the same polymer molecule. Alternatively an amount of hydrophilic polymer may comprise one or more ligands selective for Gram positive bacteria and an amount of hydrophilic polymer may provide one or more ligands selective for Gram negative bacteria.

In the case of more than one ligand, hydrophilic polymer may provide more than one indicator. One indicator may be specific for indicating sensing or detecting Gram positive bacteria by one ligand and a further indicator may be specific for indicating, sensing or detecting Gram negative bacteria by a further ligand.

Ligand may possess the facility to sense or detect Gram positive bacteria for example selected from *Staphylococcus* such as Staph. *aureus*, Staph. *epidermidis* and MRSA, *Streptococcus, Enterococcus, Corynebacterium* and *Clostridium* such as *C. difficile*, also *Peptostreptococcus, Lactobacillus, Propionibacterium, Bifidobacterium* and *Actinomyces*.

Alternatively or additionally ligand may possess the interact with facility to sense or detect Gram negative bacteria for example selected from proteobacteria such as Enterobacteriaceae for example, *Escherichia coli, Salmonella, Shigella, Pseudomonas* such as *Pseudomonas aeruginosa, Proteus, Klebsiella*, also *Legionella, Hemophilus, Neisseria, Acinetobacter* such as *A. baumannii, Bacteroides, Prevotella, Fusobacterium, Porphyromonas* and the cyanobacteria and spirochaetes.

Preferably ligand is selective for bacteria encountered in a wound environment. Such bacteria may include for example Gram negative aerobic bacteria such as *Pseudomonas aeruginosa*, Gram positive bacteria such as *Staphylococcus aureus*, more particularly MRSA (methicillin resistant *Staphylococcus aureus*) also known as ORSA (oxacilin resistant *Staphylococcus aureus*) anaerobic bacteria such as *Bacteroides fragilis*, yeast such as *Candida albicans* and fungi such as *Aspergillis braziliansis*. In an advantage ligand possesses the facility to sense or detect and optionally interact with and/or bind at least Gram positive and/or Gram negative bacteria, for example in a level of bioburden including any of contaminated, colonised, critically colonised and infection level. These levels are given the meaning known in the art.

More preferably the bacteria binding ligand is selected from one or more of vancomycin, polymyxin, beta-lactam and teicoplanin antibiotics and cationic peptides such as the cecropin and melittin hybrid, CEME and defensins and antimicrobially inactive, preferably antibiotically inactive derivatives thereof.

Bacteria binding ligand may be derived from a reactive form thereof suitable for reacting with or derivatising the hydrophilic polymer. For example polymyxin provided as a ligand to the hydrophilic polymer is derived from a modified polymyxin which is reactive with the hydrophilic polymer. Specifically polymyxin is provided in form devoid of antibiotic activity. Antibiotically inactive polymyxin is deacylated at one acyl chain thereof.

Preferably hydrophilic polymer is derivatised by the attachment of one or more peptide antibiotics.

Preferably attachment of said ligands to highly branched hydrophilic polymer is at the ends of a plurality of the polymer branches. or at a plurality of sites along the polymer backbone and at the polymer chain termini. Attachment is preferably achieved by linkage to binding groups such as for example carboxylic acid or succinimide groups. Preferably attachment is at the end of a multitude of the polymer branches or at a multitude of backbone sites and polymer chain termini. Attachment may be at substantially all of the polymer branches or backbone sites and termini or at a percentage thereof.

Preferably hydrophilic polymer for sensing or detecting and optionally binding bacteria comprises vancomycin or polymyxin or derivatives as hereinbefore defined, in a ratio of up to 35 moles ligand to 1 mole hydrophilic polymer.

It is convenient to express ligand:hydrophilic polymer as a wt:wt ratio. Preferably such ligand:hydrophilic polymer is in the range 3-30:100 wt:wt.

We have found that there is an optimum range of binding ratio at the lower end of which the hydrophilic polymer presents sufficient ligand to give a measurable response and at the upper end of which the ligand is oriented to be freely available to detect bacteria. Above this optimum range it is possible that access to ligands becomes obstructed and some ligand becomes unavailable for binding.

In an advantage, ligand present in high ratio as hereinbefore defined possesses the facility to gather or accumulate species such as bacteria by binding or interaction, in manner to create a species dominant environment in the proximity of the linear polymer. We believe that this further enhances the range of sensitivity of detection or binding, and the facility of the polymer material to provide low, intermediate and high sensitivity indication of detection and/or binding, for example of bacteria.

Orientation of ligand in relation to the copolymer is not insignificant. Hydrophilic polymer suitably comprises ligand disposed in pendant manner, for example at branch termini, along the backbone or at chain termini.

Indicator

Indicator as hereinbefore defined preferably provides indication or change in indication in the form of an optical change, a molecular or phase change, or a change in adsorption or emission signal or spectrum in the UV, visible or Infra red regions of the electromagnetic spectrum.

Indicator may indicate a change in stimulus response as a result of binding or of sensitivity to its environment induced directly or indirectly by said stimulus. Preferred indicator indicates a change in stimulus or a change in stimulus response as hereinbefore defined, such as presence or type of bacteria or change in pH, or a change in polarity or hydrophilicity.

Indicator such as dyes, imaging agents, indicating monomers and the like are known in the art and include species sensitive indicators which may sense or detect a species directly, e.g. by interaction therewith, or indirectly, e.g. by sensing or detecting a change initiated by the species, such as desolvation resulting in coil to globule transition as hereinbefore described or binding to ligand as hereinbefore defined. Suitably indicator is selected from those which are sensitive to bacteria, hydrophobic or hydrophilic or polar environments, such as their lipid-rich environment, to pH and the like.

Preferably indicator is selected from solvatochromic dyes, including fluorescent dyes, colour changing indicators, and combinations thereof and their polymerisable monomers or oligomers. Solvatochromism is the ability of a chemical substance to change color due to a change in solvent polarity. Preferred indicator includes polymerisable fluorescent solvatochromic dyes, i.e. dyes which may be incorporated as a copolymer with the hydrophilic polymer and which change fluorescence in response to a change in polarity. Solvatochromic dyes provide an change in maximum absorption and in fluorescence in response to a polar to non-polar transition. Preferred solvatochromic indicator exhibits a wide range of polar sensing.

Preferred indicators include any which are polymerisable or which may be rendered polymerisable and which exhibit fluorescent solvatochromic behaviour.

More preferably indicator is selected from one or more of the naphthalenes, phenoxazines, phenylazenes and phenylazos compounds and their derivatives, for example Dansyl cadavarine (5-amino pentyl)-5-diethylamino-1-napthalene sulphonamide)

and reactive derivatives thereof including Dansyl chloride and

N-[2[[[(5-N,N-dimethylamino)-1-naphthalenyl sulphonyl]-amino]ethyl]-2-propenamide (DANSAEP), Nile Red™ (9-diethylamino-5H-benzo[a]phenoxazine-5-one) 2-[4(2-hydroxyethylsulfonyl)-phenyl]diazenyl]-4-methylphenol, Nile Blue 5-amino-([9-(diethylamino)benzo[a]phenoxazin-7-ium) sulphonate and polymerisable forms including the corresponding acrylamide, 1-hydroxy-4-[4[(hydroxyethylsulphonyl)-phenylazo]-napthalene-2-sulphonate, 2-fluoro-4-[4[(2-hydroxyethanesulphonyl)-phenylazo]-6-methoxy phenol, 4-[4-(2-hydroxyethylsulphonyl)-phenylazo]-2,6-dimethoxyphenol, fluorescent monomers with benzofurazan skeleton, including for example 4-(2-acryloyl oxyethylamino)-7-nitro-2,1,3-benzoxadiazole (NBD-AE) and 4-(2-acryloylaminoethylamino)-7-nitro-2,1,3-benzodiazole (NBD-AA), 4-amino-1,8 napthalimide derivatives including 2-(6-(dimethylamino)-1,3-dioxo-1H-benzo(de)isoquinolin-2(3H)-yl) ethyl methacrylate and reactive derivatives and combinations thereof.

Reference herein to Nile Red™, includes its reactive derivatives in particular hydroxyl Nile Red™ 9-(diethylamino-2-hydroxy-5H-benzo[a]phenoxazine-5-one and Nile Red™ acrylate 9-(diethylamino-2-acryloyloxy-5H-benzo[a] phenoxazine-5-one. Nile Red is known as a fluorescent indicator for bacteria and intracellular lipids. Nile Red fluoresces in lipid-rich environments. Fluorescence is at different wavelength according to the polarity of the environment, and Nile Red does not fluoresce in most polar solvents. It can be readily visualised using an epifluorescence microscope.

Nile Red™ is commercially available as 9-diethylamino-5H-benzo[a]phenoxazine-5-one. Hydroxyl Nile Red™. may be obtained in known manner or Nile Red acrylate may be obtained by synthesising the hydroxyl derivative of Nile Red and reacting with acryloyl chloride for example as disclosed in Chemistry of Materials 2011, 23, 3348-3356, the contents of which are incorporated herein by reference.

The fluorescence characteristics of Nile Red™ monomer are essentially the same as Nile Red™ as follows Nile red absorbance max in water=584 nm, emission max in water=666 nm Absorbance max in cyclohexane=469 nm, emission max in cyclohexane=570 nm, ref Green Chemistry 2001, 3, 210-215

Nile Blue is commercially available as the 5-amino 9-(diethylamino)benzo[a]phenoxazin-7-ium sulphonate which may conveniently be converted to the corresponding acrylamide.

Nile blue absorbance max in water=635 nm, emission max in water=674 nm

Absorbance max in chloroform=624 nm, emission max in chloroform=647 nm,

Reference herein to Dansyl™, includes its reactive derivatives in particular Dansyl chloride. Dansyl™ is commercially available as Dansyl™ cadavarine (5-amino pentyl)-5-diethylamino-1-naphthalene sulphonamide). Dansyl cadaverine may be reacted with acryloyl chloride to give an acrylamide derivative, or may be provided as N-[2[[(5-N, N-dimethylamino)-1-naphthalenyl sulphonyl]-amino] ethyl]-2-propenamide (DANSAEP) as disclosed in Chemical Physics Letters 307 (1999) 55-61 the contents of which are incorporated herein by reference.

Dansyl cadaverine is commercially available. Dansyl acrylamide may be obtained in known manner for example as disclosed in Chemical Physics Letters 307 (1999) 55-61, the contents of which are incorporated herein by reference.

Dansyl monomer has fluorescence characteristics including absorbance max in water=329 nm, emission max in water=530 nm, absorbance max in hexane=333.7 nm, emission max in hexane=463 nm.

Fluorescent monomers with benzofurazan skeleton as hereinbefore defined may be obtained in known manner for example as disclosed in Analytical Chemistry 2003, 75, 5926-5935, the contents of which are incorporated herein by reference.

Fluorescent monomers with benzofurazan skeleton may be excited at 469 nm.

NBD-AE emission max in isobutanol 519 nm, emission max in water 535 nm

NBD-AA emission max in isobutanol 521 nm, emission max in water 536 nm 4-amino-1,8 naphthalimide derivatives as hereinbefore defined may be obtained in known manner for example as disclosed in Journal of Materials Chemistry C, 2013, 1, 6603-6612, the contents of which are incorporated herein by reference.

4-amino-1,8 naphthalimide derivatives. When polymerised with NIPAM, have an absorbance max in PBS, 20 C=448 nm, emission maximum in PBS, 20 C=544 nm, absorbance max in chloroform=422 nm, emission maximum in chloroform=513 nm.

Indicator is suitable selected by emission max in polar or non-polar environment as appropriate, comprised in a wavelength range which may be observed directly or indirectly. Suitably detection or sensing of species or stimulus causes a decrease in hydrophilicity of hydrophilic polymer to less polar, with corresponding shift in emission max.

Indicator may be positively solvatochromic, exhibiting increased emission max wavelength with increasing polarity or negatively solvatochromic, exhibiting decreased emission max wavelength with increasing polarity.

For example in a material comprising vancomycin and polymyxin ligands, indicator may comprise Nile Red derivative selective for vancomycin detection of Gram positive bacteria and Nile Blue derivative selective for polymyxin detection of Gram negative bacteria.

Preferred indicator has a narrow emission range, more preferably narrow excitation and emission ranges for example in a range of 5 up to 100 nm, more preferably 5 up to 50 nm, most preferably 2-20 nm.

Indicator may be incorporated in any desired manner in the stimulus-responsive polyurethane material, and is preferably incorporated in the highly branched hydrophilic polymer, preferably by covalent binding at a plurality or multitude of branches. Preferably indicator is provided as a copolymer with hydrophilic polymer as hereinbefore described, preferably as a copolymer of a polymerisable indicating monomer. Preferably indicator is incorporated in ratio corresponding to species-detecting functional group, for example ligand or functionality. More preferably indicator is covalently bound to a plurality or multitude of branches or of branch termini.

In a particular advantage indicator is present in an amount defined as molar ratio of hydrophilic polymer:indicator of >50:1, preferably 1000-2500:1, for example 1500-2200:1. Indicator present in such relatively low amounts provides the required sensitivity and moreover provides superior indication.

Alternatively indicating monomer may be provided as wt/wt ratio with hydrophilic monomer of 3-30:100 indicating monomer:hydrophilic monomer Use Polyurethane material such as stimulus responsive polyurethane material as hereinbefore defined may be for any use in which detection or sensing binding or indicating of a species or stimulus is desired, for example detection or sensing binding or indicating of a chemical or biological species or stimulus.

Suitably the material is for use in applications selected from medical, dental, hygiene, point of use sterilisation, sanitation, personal care, biosurveillance and packaging.

Preferably the material is for detecting and/or sensing or binding bacteria, or for detecting or sensing pH and the like.

Such uses include for example the management of wounds, hygiene and sterilisation of articles including medical and dental articles, hygiene and sterilisation of food or of fluids, including water and air, or systems for their preparation and generation such as food preparation or packaging plants, ventilation systems, water management systems, and in particular such uses for which the detection or binding of bacteria, monitoring of pH, and the like is beneficial.

Material may be in desired form suitable for the intended use, for example sheet form. Suitably polyurethane material is in the form of a block, sheet, film, membrane, layer or coating, fiber, woven or non-woven being foamed or non foamed, in particular being conformable foam block or sheet, film, membrane, woven or non-woven or layer is particularly envisaged as hereinabove described.

In a preferred embodiment material is for use as a wound dressing or part thereof, for interrogating biological fluids including wound fluid, serum, urine, as a medical or dental sponge or wipe or the like, or pH probe or sensor in such applications or independent applications.

Material for use as a wound dressing or part thereof or in interrogating biological fluids includes use for interrogating wound fluid, for example may be in form of a dipstick, lining for vacuum line or wound fluid conduit, collar for wound fluid conduit port, wound fluid filter, wound filler or top film for wound filler and the like, in particular in relation to negative pressure wound therapy (NPWT), collar for port in other applications providing at the port a moist locus or environment as hereinbefore defined, and the like.

Preferably the material comprises a wound dressing or is for use as a secondary or primary dressing in conjunction with a primary or secondary wound dressing. As a primary dressing the material may be in the form of a wound contact layer or wound filler for an absorbent, odour absorbing or like secondary dressing, for example in moist wound healing. As a secondary dressing the material may be in the form of a fluid absorption or odour absorption layer supplementary to that of a primary dressing or be in the form of a top film to retain a primary dressing in place. Such decision may be the clinician's choice. pH or presence of bacteria may be assessed upon application of and removal of the material as primary dressing from the wound. The material may be intended for positioning at or near a lower surface of a secondary dressing. The material may be the wound contacting layer for the secondary dressing. The material may be for use as a cover layer, or intermediate layer for a primary dressing In management of deep or chronic wounds, the material may be placed into the wound to detect bacteria or pH and removed from the wound intact. Foam for use with negative pressure wound dressing is particularly contemplated.

Polyurethane materials containing immobilized PNIPAM polymers may be used to detect pH or bacteria remote from the wound. For example polyurethane material may be provided in the form of a polyurethane film or polyurethane foam plug for insertion in the vacuum line of a NPWT device, for example at the entrance to a port provided on a NPWT dressing. Polyurethane material is thereby configured to contact wound fluid emanating from a wound bed to be drawn off via a vacuum line. Such wound fluid may thereby be caused to flow over or through the polyurethane material. The polyurethane material may thereby provide indication of species or stimulus in relation to the fluid.

Polyurethane material may be provided in the form of a polyurethane film for use under the drape of a NPWT dressing located over a filler material. Polyurethane material is thereby configured to contact wound fluid comprised within the filler material as a reservoir of fluid for removal via a vacuum line. The polyurethane material may thereby provide indication of species or stimulus in relation to the fluid.

Polyurethane material may be provided in the form of a polyurethane foam for use as a dip-stick or swab. Polyurethane material is thereby configured to contact wound fluid comprised in a wound locus by contact with the wound surface. The polyurethane material may thereby provide indication of species or stimulus in relation to the fluid.

Accordingly material for use as a wound dressing or part thereof or in interrogating biological fluids includes use for interrogating wound fluid, for example may be in form of a dipstick, lining or plug for vacuum line or wound fluid conduit, collar for wound fluid conduit port, wound fluid filter, wound filler or top film for wound filler and the like, in particular in relation to negative pressure wound therapy, collar for port in connection with a fluid environment and the like.

The material may be provided in shape or size or a range of shapes or sizes suitable for a wound or locus, or may be cut to size or shape. Preferably the material is in the form of a block or sheet, film or membrane for cutting to size and shape in the manufacture of material for use as hereinbefore defined for example as a wound dressing or part thereof or for use in interrogating wound fluid or other uses as hereinbefore defined.

In a particular advantage the hydrophilic polymer provides indicator and ligand or moiety distributed throughout the polyurethane network, whereby indicator and ligand or moiety are provided at any face of a sheet of polyurethane material even when cut to size or shape. This is a particular advantage when compared to material having bacterial or pH sensing function applied as a coating at a surface, and which are not active at a face exposed by cutting after coating.

The material may be for use in treating wounds which are contaminated by or susceptible to contamination by microbes as hereinbefore defined. A particularly useful application is in treating wounds contaminated by or susceptible to contamination by bacteria, yeast and/or fungi.

Wound management includes management of chronic and acute, full thickness, partial thickness, and shallow granulating exuding wounds. Wounds for which the hereinbefore defined material has particular use include for example ulcers and pressure sores such as leg ulcers; pressure ulcers; diabetic ulcers; surgical wounds; traumatic wounds; donor sites; burns such as partial thickness burns; tunnelling and fistulae wounds; wounds left to heal by secondary intent; and wounds that are prone to bleeding such as wounds that have been surgically or mechanically debrided, cavity wounds, sinus and open wounds.

The material may be intended for visual inspection or inspection with use of a suitable inspection or scanning device or reader.

The material for inspection or scanning or reading with use of an inspection or scanning device or reader configured to receive information relating to indication or change in indication and provide output information relating to microbes or pH present at a locus, with use of a device comprising interrogation means for acquiring indicating information;
a processor for processing indicating information and generating output information,
and a display or connectivity for a display for displaying output information.

Interrogation means herein is may conveniently be described as a sensor or detector, and preferably comprises a light sensor. Light sensors are known in the art and include for example charge coupled devices (CCDs) and active pixel sensors in complementary metal-oxide semiconductors (CMOS).

Interrogation means or sensor or detector may further comprise recording means such as a camera.

Interrogation means or sensor or detector is suitable for the indicating information to be acquired.

In the case that indicating information is a fluorescence signal, interrogation means or sensor or detector may additionally comprise an excitation light source. An excitation light source has the purpose of providing excitation light to fluorescent indicating means for the generation of fluorescence information, such as fluorescence emission in the form of a fluorescence reading or fluorescence signal as hereinbefore defined.

An emission filter may further be provided, suitably for the purpose of eliminating excitation light. Emission filters are known in the art of observing fluorescence. Preferably an emission filter allows passage of light in a narrow bandwidth of for example 635-660 nm, around a central wavelength for example 647 nm.

A fluorescence chamber may additionally be provided for the purpose of containing the excitation light source and an emission filter if present. A fluorescence chamber provides a controlled lighting environment for delivery of excitation light to the sensing device, receipt of emission light therefrom and control of ambient light. Preferably the fluorescence chamber excludes ambient light which might obscure excitation and emission light. The fluorescence chamber may be separate or integral with the interfacing device, a separate chamber for example may comprise a housing to receive the material.

A fluorescence chamber may be a closed chamber adapted to receive the material or comprise a skirt adapted to be located over the material Preferably a skirt is conformable or flexible. A conformable or flexible skirt may be located over material in situ at a locus and conform to the profile of the material and/or locus to exclude ambient light. In the case of wound management, a locus may be a body part of irregular shape.

A light source may be selected from one or more lasers, LEDs and the like. Light sources may emit light at same or different wavelengths. A light source may be associated with one or more filters allowing the desired wavelength emission.

A light source may comprise a light source for emission of broad spectrum light, together with an emission filter for selection of a desired wavelength excitation light, or may comprise one or more light sources for emission of a narrow bandwidth light, such as a specific narrow bandwidth light or a narrow bandwidth of a desired wavelength. For example a light source may comprise one or more LEDs emitting light in a narrow bandwidth around a central wavelength.

Preferably a light source emits light at a wavelength corresponding to the excitation wavelength of the indicating means. A suitable wavelength may be for example in the range 590 nm. Preferably the light source emits light in a narrow bandwidth of for example 580-600 nm around a central wavelength for example 590 nm.

A processor includes means to receive acquired indicating information, means to access software for processing acquired information and means to output processed information.

Means to receive acquired indicating information may comprise a wireless or wired connection. Means to access software may comprise an integral or external memory programmed with software, or internet access to remote software or a combination thereof.

A display may be an optical or digital display. A display suitably provides processed output information in optical or digital format.

Preferably a display is a visual display unit for displaying digital images, digital quantitative read out or digital text. Text may for example include instructions to the user such as "infected", "take action", "see specialist" or the like.

Conveniently a display is a display comprised in a camera which combines light detector and display in a single unit.

A display may be integral with or remote and separate from the inspection or scanning device or reader. For example the scanning device or reader may be a mobile phone or other hand held with integral display adapted to be received within the fluorescence chamber. Alternatively or additionally a display is a remote display, for example the device may provide output information to a remote display, and may comprise means to transmit output information for display. In the case of a remote display, the device comprises connectivity for a remote display, for example a socket for a wired communication cable, a socket for a communications mounting or cradle, or wireless connection means such as Bluetooth, telecoms systems, wifi or other suitable means. A remote display may comprise one or more of a VDU, TV console (optionally wall mounted), printer, a component of the material or a construct comprising the material and the like. Variants are innumerable and well known in the art of visual displays, computing and telecommunications.

Preferably an interfacing device is mobile, more preferably is hand held.

Conveniently a mobile hand held interfacing device comprises a smart phone optionally together with an excitation light source and fluorescence chamber as hereinbefore defined. Software may be provided in the form of an App whereby external software access is not required. The App may capture and process an image of the indicating information such as emission fluorescence.

The inspection and/or scanning device or reader may comprise means such as a dock, panel or slot to receive the material and directly download information relating to indication or change in indication therefrom.

Processed output information may be in the form of a map, such as a map of fluorescence intensity or a "heat map", optionally calibrated against a fluorescence intensity reference or control.

Processed output information optionally includes location and/or orientation information, subject information for example patient information, date and the like. Processed output information may be overlaid on or otherwise compared with processed output information relating to the same or different locus.

In a further aspect there is provided a method for inspecting or scanning or reading polyurethane material or a device or dressing comprising said material as hereinbefore defined comprising locating an inspection and/or scanning device or reader as hereinbefore defined in relation to the material,
activating the inspection and or scanning device to interrogate the detection and/or sensing device and
acquire indicating information for processing, optionally additionally to process indicating information, and optionally additionally to
record or store, display or transmit for display output information.

The method suitably includes classifying output information as an assessment of wound health. An assessment may be generally classified as deteriorating, stable or improving.

Processed information may be further classified for example as an assessment of localised wound health. An assessment may be generally classified as localised, moderate or extensive health status.

The method may further comprise determining a treatment plan based on the monitoring or assessment. Treatment may include for example continuing current treatment, increasing current treatment, changing treatment or seek further information on wound health.

Figure 26:
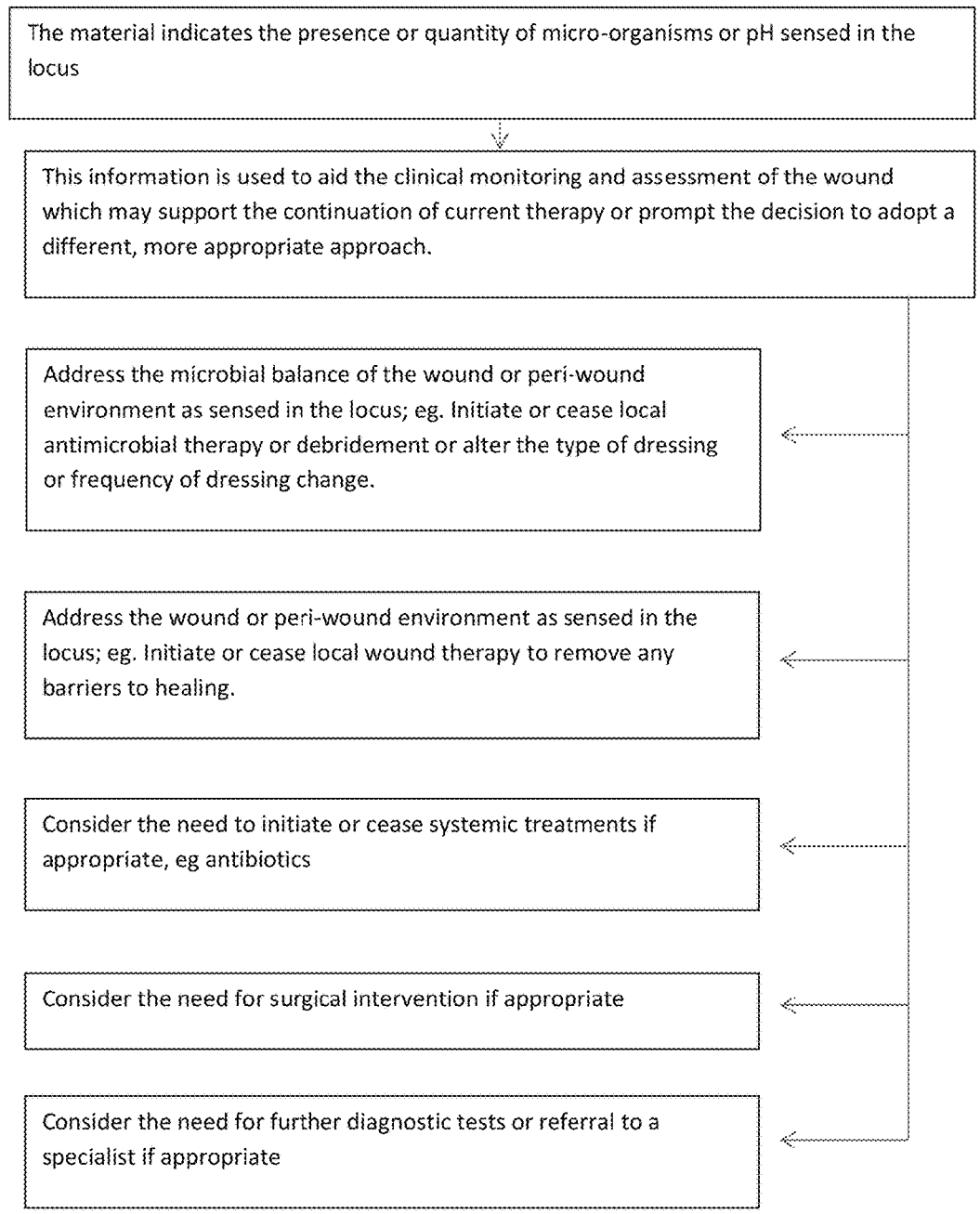
FIG. 26 illustrate a flow scheme of use of a material as an indicator on wounds.

A method is illustrated for example in the flow scheme of FIG. 26, which illustrates an example of "use of material as indicator on wounds" e.g. clinician decision resulting from different responses which might be detected.

In a further aspect there is provided a kit comprising material as hereinbefore defined, the kit further comprising a reference strip providing reference information for processing information relating to indication and change in indication and generating output information relating to bacteria or pH. Preferably a reference strip provides information to calibrate the device. For example a references strip will calibrate the device to pick up the desired wavelength of fluorescence emission and correct as necessary for processing acquired wavelength information.

A reference strip may alternatively be provided integral with material or a device or dressing as herein defined.
Device In a further aspect the invention comprises a device comprising the polyurethane material such as stimulus-responsive polyurethane material as hereinbefore defined. Preferably the device is for use as hereinbefore defined and more particularly selected from medical, dental, hygiene, point of use sterilisation, sanitation, personal care, biosurveillance and packaging. Preferably a device is for detecting and/or binding bacteria, detecting pH and the like.

In a preferred embodiment a device comprises a wound dressing or part thereof, a device for interrogation of wound fluid as hereinbefore defined, a medical or dental sponge or wipe, pH sensor or the like as hereinbefore defined. More preferably the device is for detection or sensing and/or binding of bacteria, detection or sensing of pH and the like.

Preferably a device comprises a conformable elastomeric apertured film, an intermediate conformable hydrophilic foam layer, and a continuous moisture vapour transmitting conformable polymer film outer layer in which the layers are attached in a contiguous and co-extensive relationship. In this embodiment a device may comprise a modification of commercially available hydrophilic absorbent foam, woven or non-woven fiber, film or membrane, or wound dressing comprising absorbent polyurethane foam, woven or non-woven, fiber, film or membrane. Polyurethane foams or polyurethane foam dressings which might beneficially incorporate the polyurethane material as hereinbefore defined include ALLEVYN™ foam, ALLEVYN™ Adhesive, ALLEVYN™ Gentle Border, ALLEVYN™ Gentle, ALLEVYN™ Ag Gentle Border, ALLEVYN™ Ag Gentle, PICO™ and other commercially available absorbent, hydrophilic polyurethane foams based on polyurethane polyol moieties, most particularly being compatible with the method of generating the polyurethane material as hereinbefore defined.

The invention is of particular application in providing a medical device in the form of a wound dressing comprising microbe-responsive polyurethane foam as hereinbefore defined.

Device or polyurethane material as hereinbefore defined may be sterile, and more particularly terminally sterile, as known in the art. Preferably such device or material is provided within sterilised primary packaging. Suitably the method includes optional sterilisation in known manner and packaging. Sterilisation is suitably for example by radiation such as gamma or ebeam radiation, or by thermal sterilisation.

In a particular advantage we have found that the materials and device may be provided in sterile or terminally sterile form, without deleterious effect thereon.
Method for Detecting or Sensing In a further aspect there is provided a method for detecting or sensing bacteria or pH at a locus comprising applying material as hereinbefore defined to the locus and interrogating the material to obtain an indication indicating detection or sensing of species, and optionally additionally monitoring for an indication or change in indication.

The method may comprise for example monitoring a stimulus in a subject or locus comprising applying polyurethane material such as stimulus-responsive polyurethane material as hereinbefore defined to the subject or locus and monitoring for a change in stimulus or for a stimulus response.

Interrogating or monitoring may comprise interrogating or monitoring the material directly, for example by means of the indicator.

Alternatively interrogating or monitoring comprises interrogating or monitoring of the material indirectly by means of an optical or digital reading or signal in a device for scanning or interfacing with or inspection of the material, for example with the indicator.

Preferably the method is a method for detecting microbes in or in relation to a subject or locus, comprising applying stimulus-responsive polyurethane material as hereinbefore defined to the subject or locus and monitoring for change in stimulus or for a stimulus response initiated by a microbe-binding event. Microbes are selected from bacteria, fungi and yeast.

Alternatively or additionally the method is a method for detecting pH of or in relation to a subject or locus Method of Treatment In a further aspect there is provided a method for detecting or monitoring a species or stimulus in relation to a subject or locus comprising applying polyurethane material such as stimulus-responsive polyurethane material or species indicating polyurethane material or device as hereinbefore defined to the subject or locus and detecting or sensing an indication as hereinbefore defined monitoring for an indication or a change in stimulus or for a stimulus response or for interaction or binding of species, for example directly with indicator or indirectly as a result of species binding by ligand.

Preferably the method is a method for detecting microbes in or in relation to a subject or locus, comprising applying polyurethane material such as stimulus-responsive polyurethane material or species indicating polyurethane material or device as hereinbefore defined to the subject or locus and monitoring for change in stimulus or for a stimulus response initiated by a microbe-binding eventor for detection or sensing of species. Microbes are selected from bacteria, fungi and yeast.

Preferably the method is for treatment of a wound in a subject in need thereof, wherein the wound is susceptible to microbial contamination or is suspected of being microbially contaminated, wherein monitoring is for a stimulus response induced by a microbe binding event or wherein monitoring is for interaction or binding of species for example directly with indicator or indirectly as a result of species binding by ligand.

Suitably the method includes interrogating, inspecting or scanning the microbe-responsive polyurethane material to determine binding or proximity of bacteria.

Process for Preparation
Preparation of Stimulus Responsive Polyurethane Material There is provided a process for the preparation of polyurethane material as hereinbefore defined comprising the formation of a polyurethane network wherein the network formation or part thereof is conducted in the presence of hydrophilic polymer comprising ligand or moiety and indicator as hereinbefore defined.

Preferably hydrophilic polymer is present together with an amount of network forming agent, such as chain extending agent or cross linking agent.

The polyurethane network is suitably generated from the product of reaction of polyurethane prepolymers, preferably from the reaction of prepolymers generated by the reaction of isocyanate terminated monomer and long chain diol and/or polyol.

Network forming agent may be introduced simultaneously with or subsequent to reaction of prepolymers.

Network formation suitably comprises cross linking, chain extension or the like.

Preferably the hydrophilic polymer or part or an amount thereof is in fluid phase, preferably dissolved in suitable solvent or solvated by a component of the reaction to generate polyurethane. Hydrophilic polymer may be introduced in fluid phase or may adopt fluid phase in situ. Hydrophilic polymer or an amount thereof present in part or fully dissolved or solvated form is able to form an interpenetrating or entangled network with the polyurethane polymer.

Alternatively hydrophilic polymer is provided in solid phase such as in powder form for intimate mixing in a polyurethane reaction component, such as the isocyanate, prepolymer, aqueous phase, for example a HYPOL component, a diol component or the like, optionally together with an amount of added solvent for the hydrophilic polymer.

Intimate mixing into a non-aqueous component may be conducted with simultaneous or subsequent addition of an aqueous component. Hydrophilic polymer or part or an amount thereof is thereby dissolved in the reaction component. Intimate mixing moreover provides hydrophilic polymer distributed throughout the resulting polyurethane material.

The process may comprise introducing a plurality of hydrophilic polymers as hereinbefore defined simultaneously or in sequence.

Suitably the hydrophilic polymer is combined with one or more polyurethane components prior to extrusion or casting of the combined polyurethane reaction components. Casting may be into a mould or onto a surface as known in the art. Extrusion or casting is suitably in manner to form a foamed or non foamed block or sheet, gel, membrane or film, or string, ribbon, thread or like fiber form.

It is one benefit of the invention that hydrophilic polymer may be simply blended with the polyurethane components or ingredients during the reaction thereof and prior to chain extension or crosslinking, whereby it is immobilised within the polyurethane network. Hydrophilic polymer may be blended with one of the polyurethane components or ingredients prior to combining the respective components or ingredients. For example hydrophilic polymer may be combined with an isocyanate component or polyol component or both such as the HYPOL phase or the long chain diol and/or polyol phase in a polyurethane system.

The process may be a process for preparing a foam, xerogel, film or other non-foamed material as hereinbefore defined.

There is a balance between a low water content gel necessary to preserve the immobilisation of hydrophilic polymer and the presence of water to assist in dissolving hydrophilic polymer and enable network interpenetration or entanglement. Polyurethane material may be cast, such as cast from solvent, or extruded into the above forms as known in the art.

The process may be a process for preparing stimulus-responsive polyurethane material as hereinbefore defined, preferably comprising polymerisation reaction of aromatic isocyanate monomer and long chain diol and/or polyol as hereinbefore defined, including optional step growth polymerisation, and chain extension or cross linking thereof, wherein part or all of the process is conducted in the presence of one or more highly branched hydrophilic polymer as hereinbefore defined.

The reaction may be aqueous or non aqueous.

The reaction may conveniently be illustrated in non-limiting manner as follows in Scheme a1:

Scheme a1

Polyurethane material is obtained by step growth polymerisation of diisocyanate with polyol as hereinbefore defined in the presence of hydrophilic polymer (I) as hereinbelow defined:

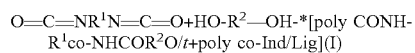

wherein $R^1$ is aromatic hydrocarbyl for example selected from toluene, methylenediphenyl, paraphenylene and naphthyl;

$R^2$ is selected from alkyl, polyester, polycaprolactone, polyether and polycarbonate;

* is highly branched hydrophilic polymer or linear hydrophilic polymer as hereinbelow defined and /t indicates terminal or in chain polymer moieties.

Preferably the process comprises step growth polymerisation as hereinbefore defined generating the corresponding isocyanate terminated oligomeric prepolymer which is simultaneously or subsequently chain extended or cross-linked. This reaction may conveniently be illustrated in non-limiting manner as follows in Scheme a2:

Scheme a2

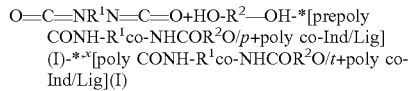
CONH-R¹co-NHCOR²O/p+poly co-Ind/Lig]
(I)-*-*[poly CONH-R¹co-NHCOR²O/t+poly co-Ind/Lig](I)

wherein variables are as hereinbefore and hereinbelow defined and

/p indicates terminal or in chain prepolymer moiety which may be the same as or different to /t; and X=crosslinker or chain extender as hereinbefore or hereinbelow defined.

Scheme a2 may be conducted as two separate steps or as a single step in which crosslinker or chain extender x is present throughout.

Polymerisation may be performed using any suitable method for example solution, suspension, emulsion and bulk polymerisation methods may all be used.

The process suitably comprises blending, optionally casting or extruding, optionally foaming, and curing as required. Preferably curing is initiated by mixing of the components Contacting may be in the presence of optional initiator, catalyst, blowing agent or foaming agent, surfactant, chain extender, cross-linker and the like as known in the art.

The polyurethane foam is suitably generated with the use of surfactants to regulate cell size and prevent collapse.

Where it is desired to prepare a foam, the process may generate foaming agent in situ. Alternatively or additionally foaming agent may be added. In situ generated foaming agent includes $CO_2$ gas generated from reaction of water and isocyanate. Added foaming agent includes $N_2$ gas and volatile liquids such as HFC-245fa (1,1,3,3-pentafluoropropane) and HFC-134a (1,1,1,2-tetrafluoroethane), and hydrocarbons such as n-pentane and the like.

Chain extenders (f=2) and cross-linkers (f=3 or greater) are suitably selected from low molecular weight hydroxyl and amine terminated compounds, as known in the art. Cross-linking agent may be selected from cross linking agents used in the preparation of foams, such as water or the like.

Polyol is commercially available in a resin or blend incorporating catalyst, surfactant, chain extender and/or cross-linker.

The process may be conducted at ambient temperature or at elevated temperature if it is desired to increase the rate of chain transfer. Preferably the process is conducted at ambient temperature up to 40 C. Elevated temperature is suitably in the range in excess of 100 C, preferably from 125 to 175 C.

The product polyurethane material, for example [poly CONH—R¹ co-NHCO R²O/t+poly co-Ind/Lig] (I), is suitably isolated from reaction medium without need for further working up. If desired however the process may optionally include in a further step washing or extraction in an aqueous solvent for the polymer, to remove residual non immobilised polymer. This may be useful in the case that hydrophilic polymer is present in a wide diversity of molecular weight, branching functionalisation or the like, whereby some polymer is entrained but is not immobilised. Preferably washing or extraction is with any solvent for the hydrophilic polymer, preferably selected from ethanol, aqueous ethanol, $CH_2Cl_2$, acetone and DMSO. Known techniques may be employed such as a series of solvent bath, nip roller and oven. Preferred solvent is aqueous ethanol. Drying may be in excess of ambient temperature for example about 6° C.

Figure 2:
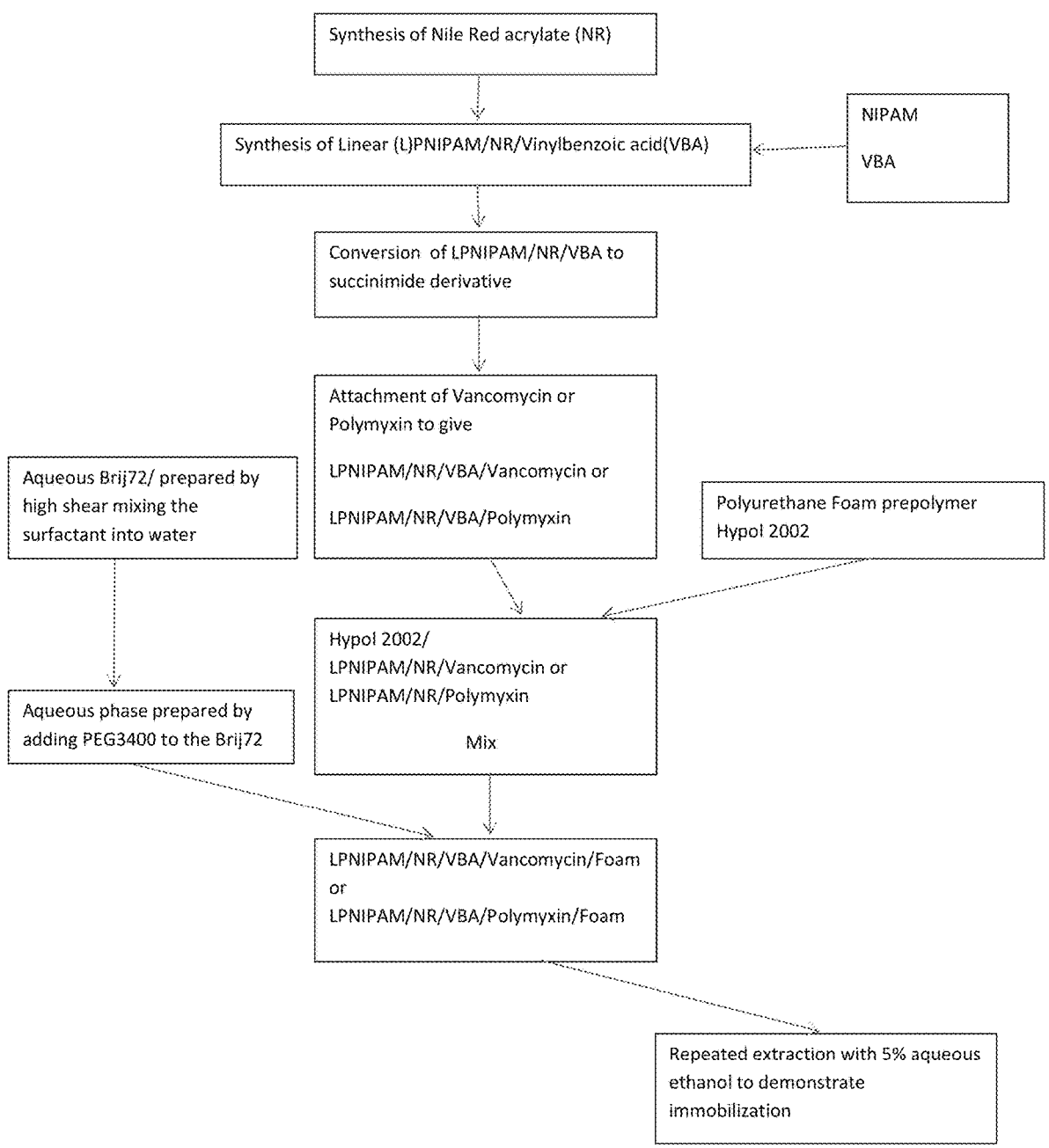

The process is illustrated in non-limiting manner in FIGS. 1-2.

Suitably the process comprises in a previous step the preparation of highly branched hydrophilic polymer as hereinbefore defined.

Preparation of Highly Branched Hydrophilic Polymer.

Preparation of highly branched hydrophilic polymer such as PNIPAM is known in the art and suitably comprises preparation from monomers of the aforementioned poly acrylamide, polyalkyl acrylamide, polyacrylate, polymethacrylate, polyacrylic acid, polymethacrylic acid, polyvinyl ether. poly vinyl caprolactam and copolymers thereof. Preparation is suitably as illustrated in FIG. 1.

Hydrophilic polymer is conveniently prepared by known radical polymerisation processes.

Preferably the polymer is prepared by controlled radical polymerisation, more preferably by reversible addition-fragmentation chain-transfer polymerisation (RAFT) employing a RAFT agent.

A RAFT agent may be selected from polymerisable dithioesters as commercially available. A RAFT agent is preferably a dithioate or dithioester such as of formula Z—C(=S)—S—R wherein Z and R are organic groups.

Suitably the radical polymerisation reaction to prepare hydrophilic polymer is conducted in the presence of indicator, such as Nile Red. This is also illustrated in FIG. 1. Nile Red is by this means incorporated in the polymer branches in desired ratio and location.

The process may be conducted at ambient temperature or at elevated temperature if it is desired to increase the rate of chain transfer. Preferably the process is conducted at elevated temperature in the range from ambient temperature up to 9° C. for example of the order of 55 to 65 C.

The thus prepared polymer incorporating indicator is suitably further reacted to introduce reactive end groups for covalent bonding to ligand for binding and/or detection of species, for example vancomycin or polymyxin. Reactive end groups are suitably selected from succinimide, generated by reaction with N-hydroxy succinimide and dicyclohexyl carbodiimide.

The reaction may conveniently be illustrated in non-limiting manner as follows in Scheme b (i)-(iii):

In step i) Functional indicator copolymer (I) is obtained from hydrophilic polymer-indicator-copolymer (II):

Scheme b (i)

wherein

HBpoly indicates highly branched polymer as hereinbefore defined such as HBpolyNIPAM;

Ind is an indicator as hereinbefore defined such as Nile Red (NR);

co- indicates a copolymer of poly and Ind;

$L^1$ is reactive functionality such as succinimide moiety;

/ indicates one or more terminal moieties; and

Lig represents functional ligand as hereinbefore defined.

Preferably in step ii) reactive hydrophilic polymer-indicator-copolymers (II and II') are obtained by interconversion from hydrophilic polymer-indicator-RAFT polymer (III)

Scheme b (ii)

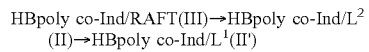

wherein HBpoly, co-, Ind, /, RAFT and $L^1$ are as hereinbefore defined and $L^2$ is reactive functionality such as carboxylic acid moiety.

Preferably in step iii) hydrophilic polymer-indicator-RAFT polymer (III) is obtained by radical polymerisation from monomer (IV) and RAFT agent (V) in the presence of reactive Indicator (VI):

Scheme b (iii)

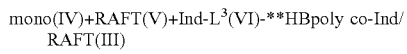

mono(IV)+RAFT(V)+Ind-L³(VI)-**HBpoly co-Ind/RAFT(III)

wherein Ind, HBpoly, co- and/are as hereinbefore defined; and mono is any monomer for preparing hydrophilic polymer as hereinbefore defined;

RAFT is any suitable dithioate or dithioester such as eg 4-vinylbenzyl-pyrrolecarbodithioate;

$L^3$ is reactive functionality such as acrylate;

** is initiator such as AVCA as hereinbefore defined.

Conditions are as described above and as known in the art.

If it is desired to introduce indicator towards or at chain ends, in a variant of scheme b, Ind is introduced during or after step iii).

The process is further illustrated in non-limiting manner in FIG. 1.

Preparation of Linear Hydrophilic Polymer.

Preparation of linear hydrophilic polymer such as PNIPAM is known in the art and suitably comprises polymerisation from monomers of the aforementioned poly acrylamide, polyalkyl acrylamide, polyacrylate, polymethacrylate, polyacrylic acid, polymethacrylic acid, polyvinyl ether. poly vinyl caprolactam and copolymers thereof.

Polymerisation is suitably conducted together with agent for attachment of functional ligand. Attachment agent is conveniently introduced pendant to the linear polymer chain, for example is introduced in the form of a pendant copolymer with the above monomer.

Attachment agent is for example vinyl benzoic acid (VBA)

Initiator for the polymerisation reaction may be present, and is suitably selected from AVCA.

Suitably the reaction to prepare linear polymer is conducted in the presence of indicator, such as Nile Red. Nile Red is thus incorporated along the polymer chain, pendant thereto in desired ratio as hereinbefore defined.

The process may be conducted at ambient temperature or at elevated temperature if it is desired to increase the rate of chain transfer. Preferably the process is conducted at elevated temperature in the range from 40 C up to 80 C, for example of the order of 55 to 65 C.

The linear polymer incorporating indicator and attachment agent is suitably interconverted to form for covalent bonding to ligand, for example vancomycin or polymyxin. Interconversion suitably replaces attachment agent with reactive groups selected from succinimide, generated by reaction with N-hydroxy succinimide and dicyclohexyl carbodiimide.

The reaction may conveniently be illustrated in non-limiting manner as follows in Scheme b (i)-(iii):

In step i) hydrophilic polymer-indicator-ligand copolymer (I) is obtained from hydrophilic polymer-indicator-copolymer (II):

Scheme b (i)

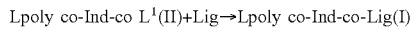

Lpoly co-Ind-co L¹(II)+Lig→Lpoly co-Ind-co-Lig(I)

wherein

Lpoly indicates linear polymer as hereinbefore defined such as LpolyNIPAM;

Ind is an indicator as hereinbefore defined such as Nile Red (NR);

co- indicates a copolymer;

$L^1$ is reactive functionality such as succinimide moiety; and

Lig represents functional ligand as hereinbefore defined.

Preferably in step ii) reactive hydrophilic polymer-indicator-copolymer (II) is obtained by interconversion from hydrophilic polymer-indicator-attachment agent (III)

Scheme b (ii)

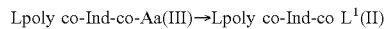

Lpoly co-Ind-co-Aa(III)→Lpoly co-Ind-co L¹(II)

wherein Lpoly, co-, Ind, and $L^1$ are as hereinbefore defined and Aa is attachment agent such as VBA.

Preferably in step iii) hydrophilic polymer-indicator-attachment agent (III) is obtained by polymerisation from monomer (IV) and attachment agent (V) in the presence of reactive Indicator (VI):

Scheme b (iii)

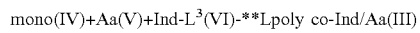

mono(IV)+Aa(V)+Ind-L³(VI)-**Lpoly co-Ind/Aa(III)

wherein Ind, Lpoly, Aa, co- are as hereinbefore defined; and mono is any monomer for preparing hydrophilic polymer as hereinbefore defined;

Aa is any suitable attachment agent such as VBA;

$L^3$ is reactive functionality such as acrylate;

** is initiator such as AVCA as hereinbefore defined.

Conditions are as described above and as known in the art.

If it is desired to introduce indicator towards or at chain ends, in a variant of scheme b, Ind is introduced during or after step iii).

The process is illustrated in non-limiting manner in FIG. 2. A number of classes of hydrophilic polymers may be produced:

I. Linear polymers with pendant indicator

II. Highly branched polymers with pendant indicator through out the polymer

III. Highly branched polymers with indicator in inner chain segments

IV. Highly branched polymers with indicator in outer linear segments

V. Highly branched polymers with indicator in outer branched segments

VI. Highly branched polymers with indicator attached to the chain ends

Indicator is preferably selected from Nile Red and Nile Blue

Here each class shows the existence of the indicator in a different location across the polymer chain, this indicator can be used to show the specific environment across that part of the polymer. Nile blue present in Class VI may equally be used as a substitute for nile red in other classes.

Figure 3:
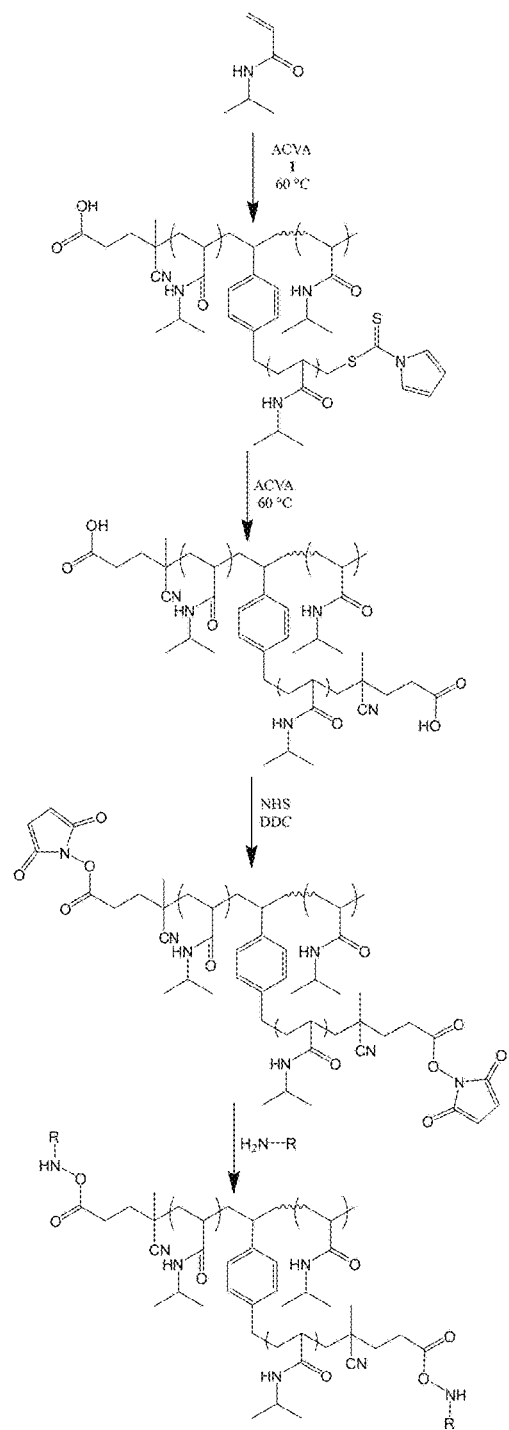
FIG. 3 illustrates a scheme for the preparation of herein defined hydrophilic polymer comprising ligand and indicator.
Figure 4:
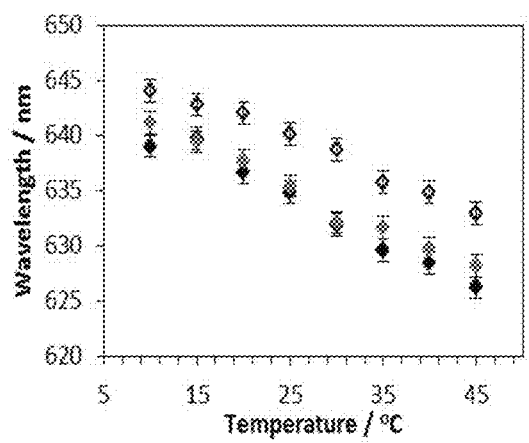
FIG. 4 illustrates LCST effect of extended hydrophilic polymer architecture.

The linear polymers (class I) were prepared by copolymerizing NIPAM, nile red acrylate and vinyl benzoic acid. Then the carboxylic acid groups were modified by reaction with vancomycin (pH 9) via the N-hydroxy succinimide (NHS) ester. The highly branched polymers were produced using modifications of the technique illustrated in FIG. 3. These class II polymers were prepared by copolymerizing NIPAM, nile red acrylate and 4-vinylbenzyl-pyrrolecarbodithioate (VBP), followed by modification of the end groups to carboxylic acid and then conjugation of vancomycin, via the NHS ester, to the end groups.

Class III, IV and V polymers were prepared by a stepwise chain extension of HB-PNIPAM: i.e. in step 1 a polymerization similar to class II polymerization was performed then in step 2 a second monomer feed was polymerized by transfer to the dithioate chain ends that are produced in the SCVP-RAFT process. In class III polymers nile red acrylate was included in the first step and not in the second step, class IV polymers included nile red acrylate only in second step polymerization that the branching monomer (VBP) and in class V the second step monomer feed included nile red acrylate, NIPAM and VBP.

Class VI polymers were made by attachment of Nile Blue to succinimide polymer chain ends via the NHS coupling reaction.

Method for Manufacture of Device

In a further aspect the invention comprises a method for the manufacture of a device comprising the polyurethane material such as stimulus-responsive polyurethane material or species indicating polyurethane material as hereinbefore defined, comprising providing said material and shaping thereof, with optional sterilisation in known manner.

Method of Treatment

In a further aspect there is provided a method for detecting or monitoring a species or stimulus in relation to a subject or locus comprising applying polyurethane material such as stimulus-responsive polyurethane material or species indicating polyurethane material or device as hereinbefore defined to the subject or locus and monitoring for an indication or a change in stimulus or for a stimulus response or for interaction or binding of species, for example directly with indicator or indirectly as a result of species binding by ligand.

Monitoring may comprise monitoring the material directly, for example by means of the indicator.

Alternatively monitoring comprises monitoring of the material indirectly by means of an optical or digital reading or signal in a device for scanning or interfacing with the material, for example with the indicator.

Preferably the method is a method for detecting microbes in or in relation to a subject or locus, comprising applying polyurethane material such as stimulus-responsive polyurethane material or species indicating polyurethane material or device as hereinbefore defined to the subject or locus and monitoring for change in stimulus or for a stimulus response initiated by a microbe-binding eventor for detection or sensing of species. Microbes are selected from bacteria, fungi and yeast.

In a further aspect there is provided a method for treatment of a subject in need thereof comprising applying polyurethane material such as stimulus-responsive polyurethane material or species indicating polyurethane material or device as hereinbefore defined to the subject and monitoring for change in stimulus or for stimulus response or for sensing or detection of species or stimulus.

Preferably the method is for treatment of a wound in a subject in need thereof, wherein the wound is susceptible to microbial contamination or is suspected of being microbially contaminated, wherein monitoring is for a stimulus response induced by a microbe binding event or wherein monitoring is for interaction or binding of species for example directly with indicator or indirectly as a result of species binding by ligand.

Suitably the method includes inspecting or scanning the microbe-responsive polyurethane material to determine binding or proximity of bacteria.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

The invention is now illustrated in non-limiting manner by the following Examples and Figures.

EXAMPLES

In the following examples/notation indicates copolymer, and is not an indication of terminal functionality.

1. Hydrophilic (highly branched (HB), linear (L) or extended (combined branch ratio or combined HB/L)) copolymer was polymerised incorporating dye (Nile Red, dansyl etc) label along the polymer chain and functionalised by having branch or linear termini functionalised with antibiotics vancomycin and/or polymyxin.

2. Hydrophilic (highly branched, linear, or extended) polymer was then mixed in with polyurethane prepolymer (polyol and isocyanate) under step growth polymerisation conditions with foaming.

3. Subsequent extraction studies were conducted to determine whether hydrophilic polymer leached from, or indeed could be extracted from, the thus formed PU foam. Nile Red label facilitated visualisation of HB polymer in relation to the polyurethane foam and to extraction washings isolated from the foam.

1. Synthesis of Highly Branched and Highly Branched Extended Copolymers 1.1 Synthesis of
4-Vinylbenzyl-pyrrolecarbodithioate (RAFT Agent)

Sodium hydride (11.92 g) was added to a dry 500 ml three necked round bottomed flask together with 160 ml DMF. Pyrrole (20 g) in 10 ml DMF was added to the rapidly stirring mixture over a 30 minute period. The mixture was stirred for a further 30 minutes and then cooled to 0 C in an ice bath. Carbon disulphide (18 ml) in 10 ml DMF was added dropwise over to minutes and the solution stirred for 30 minutes and then cooled to 0 C. 4-vinyl benzoic acid (45.48 g) in 10 ml DMF was added dropwise over 20 minutes and the mixture stirred overnight at room temperature. The mixture was split in two and transferred to a separating funnel and 80 ml diethyl ether and 80 ml water added. The organic layer was recovered and the aqueous layer extracted 3 times with ether. This process was repeated for the other half and ether extracts were combined and dried with magnesium sulphate. The solvent was removed by rotary evaporation to give a red/brown oil. The crude RAFT agent was purified by column chromatography using petroleum spirit 40-60 C as the eluent. The solvent was removed by rotary evaporation to give a bright yellow oil that solidifies around room temperature. The yield was typically ~50-60%.

1.2 Synthesis of Nile Red Acrylate (5-Diethylamino)-2-Nitrosophenol Hydrochloride 3-Diethylaminophenol (5 g) was dissolved in a mixture of concentrated HCl (11 ml) and water (6 ml) and cooled on ice. A solution of sodium nitrite (2.1 g) in water (35 ml) was added dropwise over 1 hour and the resulting slurry stirred on ice for a further 2 hours. The crude product was dissolved in boiling ethanol and recrystallized with diethyl ether to yield a yellow/orange solid (3.7 g, 50% yield). Mass spectrometry found m/z=195, expected 195.

9-Diethylamino-2-hydroxy-5H-benzo[R]phenoxazin-5-one Hydroxy Nile Red

5-Diethylamino-2-nitrosophenol hydrochloride (1.5 g) and 1,6-dihydroxynaphthalene (1.05 g,) were dissolved in DMF (180 ml) and refluxed for 7 hours. The solvent was removed and the residue purified by silica gel column chromatography (petroleum spirit:ethyl acetate 20%-100%) yielding 0.52 g (20%) of a dark blue solid. $^1$H NMR in DMSO d6: d=10.4 (1H, s), 7.95 (1H, d), 7.88 (1H, d), 7.6 (1H, d), 7.08 (1H, d), 6.8 (1H, d), 6.6 (1H, d), 6.15 (1H, s), 3.5 (4H, q), 1.18 (6H, t). Mass spectrometry found m/z=335, expected 335.

Nile Red Acrylate

Hydroxy nile (0.5 g) was dissolved in dichloromethane (140 ml) and triethylamine (870 ml) and acryloyl chloride (500 ml) added. The solution was stirred at room temperature for 7 hours. Solvent was removed and the residue purified by silica gel column chromatography (petroleum spirit:ethyl acetate (2:1) yielding 0.2 g (34%). $^1$H NMR in DMSO d6: d=8.3 (1H, d), 8.2 (1H, d), 7.6 (1H, d), 7.5 (1H, d), 6.85 (1H, d), 6.75 (1H, d), 6.6 (1H, d), 6.5 (1H, q), 6.3 (1H, s), 6.2 (1H, d), 3.5 (4H, q), 1.2 (6H, t). mass spectrometry found m/z=389, expected 389.

1.3 Highly Branched PolyN-Isopropyl Acrylamide by RAFT Polymerisation

HB-PNIPAM was prepared with different degrees of branching as follows:

1.3.1 15:1 NIPAM:RAFT Agent, Nile Red Copolymer 10 g N-isopropyl acrylamide, 1.53 g RAFT agent (1.1 above), 1.65 g 4,4'-azobis(4-cyanovaleric acid (ACVA, initiator), 0.02 g nile red acrylate dissolved in 50 ml dioxane were added to a glass ampule. Following degassing the ampule was flame sealed and placed in a waterbath at 6° C. for 48 hours. The polymer was obtained by precipitation into diethyl ether and filtered to give a pink powder.

1.3.2 25:1 NIPAM:RAFT Agent, Nile Red Copolymer (0.2% and 0.4% Nile Red)

10 g N-isopropyl acrylamide, 0.91 g RAFT agent, 0.99 g ACVA, 0.02 g nile red acrylate dissolved in 50 ml dioxane were added to a glass ampule. Following degassing the ampule was flame sealed and placed in a waterbath at 60 C for 48 hours. The polymer was obtained by precipitation into diethyl ether and filtered to give a pink powder.

The corresponding copolymer 1.3.2.1 was prepared in the same manner using 0.04 g nile red acrylate.

1.3.3 45:1 NIPAM:RAFT Agent, Nile Red Copolymer 10 g N-isopropyl acrylamide, 1.53 g RAFT agent, 1.65 g ACVA, 0.02 g nile red acrylate dissolved in 50 ml dioxane were added to a glass ampule. Following degassing the ampule was flame sealed and placed in a waterbath at 60 C for 48 hours. The polymer was obtained by precipitation into diethyl ether and filtered to give a pink powder.

1.3.4 Synthesis of Highly Branched Extended Copolymers 1.3.4.1 15:1 NIPAM:RAFT Agent Core, 15:1 NIPAM:RAFT Agent Nile Red Outer Extended Copolymer The corresponding copolymer with Nile Red in the outer only was prepared from 5 g 15:1 NIPAM:RAFT copolymer obtained using the methodology 1.3.1 above modified by omission of Nile Red, combined with 5 g N-isopropyl acrylamide, 0.77 g RAFT agent and 0.83 g ACVA, and 0.01 g Nile Red.

1.3.4.2 25:1 NIPAM:RAFT Agent Core, 25:1 NIPAM:RAFT Agent Nile Red Outer Copolymer The corresponding copolymer with Nile Red in the outer only was prepared from 5 g 25:1 NIPAM:RAFT polymer obtained using the methodology 1.3.2 above modified by omission of Nile Red, combined with 5 g NIPAM, 0.45 g RAFT agent, 0.5 g ACVA and 0.01 g nile red acrylate.

1.3.5 Synthesis of Copolymers with Variant Dyes 1.3.5.1 NIPAM:RAFT Agent, Dansyl Copolymer The corresponding copolymer with Dansyl was prepared by analogy with the above methodologies, using dansyl acrylamide in place of nile red acrylate.

1.3.6 Synthesis of Copolymers with Variant Monomers 1.3.6.1 25:1 EPAM:RAFT Agent, Nile Red Copolymer The corresponding copolymer with ethyl acrylamide monomer was prepared by analogy with the above methodology (1.3.2) using ethyl acrylamide in place of n-isopropyl acrylamide.

1.3.6.2 25:1 (EPAM/NIPAM 50/50):RAFT Agent, Nile Red Copolymer

The corresponding copolymer with ethyl acrylamide monomer was prepared by analogy with the above methodology (1.3.2) using ethyl acrylamide in place of n-isopropyl acrylamide.

1.4 Synthesis of Linear and Linear Extended Copolymers 1.4.1 Linear Polymer: Copolymer of N-Isopropyl Acrylamide and Vinyl Benzoic Acid and Nile Red 6 g N-isopropyl acrylamide, 0.31 g vinyl benzoic acid, 0.155 g ACVA, 0.012 g nile red acrylate dissolved in 37 ml dioxane, 7.5 ml dimethyl formamide were added to a glass ampule. Following degassing the ampule was flame sealed and placed in a waterbath at 6° C. for 48 hours. The polymer was obtained by precipitation into diethyl ether and filtered to give a pink powder.

1.4.2 25:1 NIPAM:RAFT Agent Core, Linear Nile Red Outer Extended Copolymer

The corresponding copolymer with branched core and linear outer with Nile Red in the outer only was prepared from 6 g 25:1 NIPAM:RAFT polymer obtained using the methodology 1.3.2 above modified by omission of Nile Red, combined with 6 g NIPAM, 0.31 g vinyl benzoic acid, 0.155 g ACVA and 0.012 g nile red acrylate using the methodology of 1.4.1 above.

1.5 Attachment of Vancomycin to Polymers 1.5.1 Attachment to 15:1 Polymer

Conversion of Chain Ends to Carboxylic Acid 3 g of RAFT polymer was dissolved in 25 ml DMF and heated to 65 C. Three additions of ACVA (10 g on each occasion) were made over 72 hours after which time the polymer was recovered by precipitation into diethyl ether and further purified by ultrafiltration. After rotary evaporation a red solid was obtained.

Conversion of Chain Ends to Succinimide.

1.5 g carboxylic acid terminated polymer was dissolved in 200 ml DMF. 0.4225 g N-hydroxy succinimide and 0.453 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 200 mg of succinimide derivatised polymer was dissolved in 10 ml water over ice and 120 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.2 Attachment to 25:1 Polymer

Conversion of Chain Ends to Carboxylic Acid 3 g of RAFT polymer was dissolved in 25 ml DMF and heated to 65 C. Three additions of ACVA (5.9 g on each occasion) were made over 72 hours after which time the polymer was recovered by precipitation into diethyl ether and further purified by ultrafiltration. After rotary evaporation a red solid was obtained.

Conversion of Chain Ends to Succinimide.

1.5 g carboxylic acid terminated polymer was dissolved in 200 ml DMF. 0.255 g N-hydroxy succinimide and 0.453 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 250 mg of succinimide derivatised polymer was dissolved in 10 ml water over ice and 100 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.3 Attachment to 45:1 Polymer

Conversion of Chain Ends to Carboxylic Acid 3 g of RAFT polymer was dissolved in 25 ml DMF and heated to 65 C. Three additions of ACVA (3.24 g on each occasion) were made over 72 hours after which time the polymer was recovered by precipitation into diethyl ether and further purified by ultrafiltration. After rotary evaporation a red solid was obtained.

Conversion of Chain Ends to Succinimide.

1 g carboxylic acid terminated polymer was dissolved in 15 ml DMF. 0.094 g N-hydroxy succinimide and 0.1.66 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 250 mg of succinimide derivatised polymer was dissolved in 10 ml water over ice and 112 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.4 Attachment to Linear polyNIPAM-Co-VBA

Conversion of Carboxylic Acid Groups to Succinimide 1.5 g of polymer was dissolved in 20 ml DMF. 0.255 g N-hydroxy succinimide and 0.453 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 300 mg of succinimide derivatised polymer was dissolved in 10 ml water over ice and 135 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.5 Attachment to Extended Copolymers with Variant Dyes 1.5.5.1 15:1 NIPAM:RAFT Agent Core, 15:1 NIPAM:RAFT Agent Nile Red Outer Copolymer The copolymer 1.3.4.1. was derivatised with vancomycin in the same way as copolymer 1.5.1 above to give vancomycin chain ends.

1.5.5.2 25:1 NIPAM:RAFT Agent Core, 25:1 NIPAM:RAFT Agent Nile Red Outer Copolymer The copolymer 1.3.4.2. was derivatised with vancomycin in the same way as copolymer 1.5.2 above to give vancomycin chain ends.

1.5.5.3 25:1 NIPAM:RAFT Agent Core, Linear Nile Red Outer Extended Copolymer

The copolymer 1.4.2. was derivatised with vancomycin in the same way as copolymer 1.5.4 above to give vancomycin chain ends.

1.5.6 Attachment to Copolymers with Variant Dyes 1.5.6.1 NIPAM:RAFT Agent, Dansyl Copolymer The copolymer 1.3.5.1 was derivatised with vancomycin in the same way as copolymers 1.5 above to give vancomycin chain ends.

1.5.7 Attachment to Copolymers with Variant Monomers 1.5.7.1 25:1 EPAM:RAFT Agent, Nile Red Copolymer The copolymer 1.3.6.1 was derivatised with vancomycin in the same way as copolymer 1.5.2 above to give vancomycin chain ends.

1.5.7.2 25:1 (EPAM/NIPAM 50/50):RAFT Agent, Nile Red Copolymer

The copolymer 1.3.6.2 was derivatised with vancomycin in the same way as copolymer 1.5.2 above to give vancomycin chain ends.

1.6. Attachment of Polymyxin to Polymers

Modification of Polymyxin B Sulphate 200 mg fluoronylmethyloxycarbonyl chloride FMOC (200 mg) was added to 5 ml IM sodium carbonate solution and mixed with 500 mg polymyxin sulphate B dissolved in 10 ml water and stirred for 24 hours. The resulting solid was filtered and washed with water and then dried.

200 mg of FMOC-polymyxin in 20 ml TRIS buffer was mixed with 8 mg polymyxin acylase in 8 ml phosphate buffered saline pH8 and stirred overnight. The product was filtered and washed with water.

Attachment of polymyxin to hyperbranched polymers with succinimide derivatised chain ends 1.6.1 Attachment to 25:1 Polymer 300 mg of polymer was dissolved in 5 ml DMF. 100 mg of derivatised polymyxin was added and the solution was stirred for 48 hours. The solution was poured into 100 ml of water together 10 ml 20% aqueous pipiridine to cleave the protecting FMOC groups. The polymer was purified by ultrafiltration and freeze dried to give a pink solid.

1.6.2 Attachment to 45:1 Polymer 250 mg of polymer was dissolved in 5 ml DMF. 75 mg of derivatised polymyxin was added and the solution was stirred for 48 hours. The solution was poured into looml of water together 9 ml 20% aqueous pipiridine to cleave the protecting FMOC groups. The polymer was purified by ultrafiltration and freeze dried to give a pink solid.

1.6.3 Attachment without FMOC

Attachment was carried out without FMOC protection, at low pH and under dilute conditions.

2. Immobilisation of Synthesised Copolymers in Polyurethane Material

2.1 Generation of HBPNIPAM/Vancomycin/Nile Red Immobilised PU Foam

Materials
 PNIPAM/Nile Red/van (1.5 above)
 Hypol 2002 (isocyanate solution): Batch no 21.8.12 (Smith & Nephew)
 Brij solution: Batch no 21.8.12 (Smith & Nephew)
 THF: Batch no STBD2989V (Sigma)

2.1.1 Method

Step 1. Hypol 2002 (batch no. 21.8.1, stored at 38 C, 10 g) was weighed into a small 60 ml plastic container and PNIPAM/Nile Red polymer (0.5 g, powder or dissolved in THF 5 ml) was added and mixed thoroughly, and then placed in the incubator for approximately 5 minutes.

Step 2. The aqueous phase (Brij solution) was weighed (8.5 g) into a small 60 ml plastic pot.

Step 3. The Hypol/polymer mix was removed from the incubator and the aqueous phase immediately added, and the mixture stirred rapidly with a spatula, until the two phases had created a creamy emulsion (approximately 10-15 seconds).

Step 4. The emulsion was poured into a clean 60 ml container and allowed to foam.

Step 5. After approximately 15 minutes once the foam had cured to a non-tacky elastomeric foam, it was removed from the container and dried at 40-5° C. overnight in a vacuum oven set at 20 mbar.

2.1.2 Method

Steps 1-5 of Method 2.1.1 were followed with the following adaptation: Step 1. Hypol (5 g) placed in an incubator.

Step 2. Brij (5 g), PEG 3400 (40 mg) and PNIPAM/Nile Red vancomycin copolymer (0.25 g) mixed together and placed in fridge to cool.

Step 3-5 as Method 2.1.1.

Steps 1 to 5 of the above Methods were repeated using the following quantities of HB-PNIPAM sample polymers, Hypol and aqueous phase:

| Foam | Sample/g | Hypol/g | Aqueous phase/g |
| --- | --- | --- | --- |
| 2.1.1.1 | 1.5/0.28 | 5 | 4.25 |
| 2.1.1.2 | 1.5/0.29 | 5 | 4.25 |
| 2.1.1.3 | 1.5.2/0.5 | 5 | 5 (+40 mg PEG3400) |
| 2.1.1.4 | 1.5.2/0.25 | 5 | 5 (+40 mg PEG3400) |
| 2.1.1.5 | 1.6.3/0.2 | 5 | 4.5 (+10 mg PEG3400) |
| 2.1.1.6 | 1.5.6.1/0.2 | 5 | 4.5 (+10 mg PEG3400) |
| 2.1.2.1 | 1.5.2/0.25 | 5 | 5 (+40 mg PEG3400) |

In all cases and in all subsequent immobilisations, the copolymer was incorporated without affecting the foaming reaction. Good quality foams were obtained with uniform pink colour or (2.1.1.6-Dansyl) cream colour, showing the dye evenly dispersed in the foam.

2.2 Generation of HBPNIPAM/Vancomycin/Nile Red Immobilised PU Film

Materials
 HBPNIPAM/Nile Red/van (1.5 above)
 Hypol 2002 (isocyanate solution): Batch no 857370 (Smith & Nephew)
 THF (Sigma Aldrich Batch no STBB0055H9)
 Tin octoate Sigma Aldrich Batch no SLBC8056V
 Butane diol Sigma Aldrich Batch no STBF1852V 2.2.1 Method Step 1. Hypol (5 g) heated to 4° C. for ease of handling and tin octoate (0.5 ml) were dissolved in THF (40 ml). Butane diol (0.227 g) in THF (10 ml) was added and the solution refluxed for 5 hours.

Step 2. HBPNIPAM/Nile Red polymer (0.5 g, dissolved in water/THF (1 ml/2 ml) was added to the HYPOL/butane diol solution and refluxed for a further hour.

Step 3. The Hypol/polymer solution was allowed to cool.

Step 4. The cooled Hypol/polymer solution was poured onto siliconized release paper.

Step 5. Solvent was allowed to evaporate. The resulting film was washed using established procedure.

2.2.1 Results

A pink colored film was obtained. Further extraction produced clear washings indicating that PNIPAM was successfully immobilised in the film.

2.3 Generation of HBPNIPAM/Vancomycin/Nile Red Immobilised PU Xerogel Adhesive Materials
 As 2.2 above 2.3.1 Method Step Pre 1. Generation of Prepolymer: A polyoxyethylene-polyoxypropylene diol monobutyl ether, which has a ratio of polyoxyethylene to polyoxypropylene residues of 1:1 and molecular weight of 4095 {300 g, 0.073 moles based on OH value) and a polymeric methylene diphenyl diisocyanate (3721 g, 0.266 moles, —NCO functionality of 2.7) were mixed together at an NCO/OH ratio of 2.5 in a 700 cm$^3$ flange flask fitted with an overhead stirrer.

The flask was heated in a waterbath set to a temperature of 90° C.

A catalyst comprising dibutyl tin dilaurate {0.2% w/w) was added. The mixture was stirred at 90° C. for two hours.

The prepolymer so formed was allowed to cool. The prepolymer was a golden yellow viscous liquid which may be stored in a capped bottle until ready for use.

The prepolymer was found to have an isocyanate content of 1.98%.

Step 1. HBPNIPAM/Nile Red polymer is dissolved in prepolymer from Step Pre 1, used in place of HYPOL of Method 2.1.1.

Steps 2-3 of Method 2.1.1 and Steps 4-5 of Method 2.2.1 are followed with the following adaptation:

Step 2 of Method 2.1.1. A glycol used in place of the Brij solution. A portion of the prepolymer and the calculated quantity of glycol which would react with all the available isocyanate are mixed at room temperature until homogeneous.

Step 3 as Method 2.1.1.

Step 4 as Method 2.2.1. The prepolymer PNIPAM diethyleneglycol then spread onto a silicone release paper at a weight per unit area of 280 gsm and cured at 90° C. to give an adhesive mass.

Step 5 as Method 2.2.1. The adhesive mass contains 85% by weight of water when fully hydrated.

A precast film of a thermoplastic polyether polyurethane may be transfer coated onto the adhesive mass. and the laminate strip so formed cut into pieces which are suitable for adhesive dressings and packed in a bacteria proof and waterproof package and sterilised by irradiation.

2.3.2 Method

Step 1 as Method 2.3.1 except that polyoxyethylene/polyoxyproylene glycol is reacted with Desmodur N100, a solvent free aliphatic polyisocyanate, essentially 3 functional, in a molar ratio of 2:1 to form a prepolymer.

3. Immobilisation and Extraction Studies; Hydrophilic Response and Sterilisation Aim:

This example shows the immobilisation of branched polymer in the polyurethane network. The hydrophobic response of the immobilised branched polymer was maintained as evidenced by change in Nile red coloration in different solutions. 5 washings were found to be effective in removing residual non-bound polymer. UV and compiled peak wavelengths of aqueous EtOH and pure EtOH washings of HBPNIPAM polymers immobilised in foam (eg ALLEVYN foam) were analysed.

Example 3.1/Solvent Extraction Aqueous Ethanol

Three polymers produced by the above methodology were incorporated into foam during the foaming process. These foams were then washed and the washing solution analysed to determine if any of the polymers had leached out of the foam. The foams were also tested in different hydrophilic environments to determine the effect of hydrophobicity on the foams.

Samples 3.1.1 HBPNIPAM/Nile red copolymer immobilised PU foam, RAFT agent still attached 3.1.2 HBPNIPAM polymer immobilised PU foam, RAFT agent removed to give carboxyl functionality contains, fluorescent tag 3.1.3 HBPNIPAM polymer immobilised PU foam, RAFT agent removed to give carboxyl functionality Aqueous/Ethanolic Extracts of Polymer Foams 1. Samples of each of the foams (0.5 g) were placed in plastic containers (60 ml) and 5% aqueous ethanol (20 ml) added
2. The mixture was agitated using an orbital shaker and left for 2 hours
3. The foams were removed from the liquid and squeezed to release as much solution as possible
4. The extracted solution were then tested using UV spectral analysis, the following samples were analysed Control foam was made and washed in addition to the polymer foams. The UV spectra of the washes from the control foam gave an indication of any residues that are washed out of standard foams, and can be used to determine any differences seen with the polymer foams wash spectra. The UV spectra showed washes 1 and 2 carried out using 5% aqueous ethanol and a wash carried out in ethanol. All three spectra for the control foam had a peak with a maxima between 284.49 nm and 285.48 nm, hence for any foam that was washed in these conditions a peak in or close to this region would be expected.

The polymer was successfully immobilised into foam and only a small amount of the appeared to wash out. The polymers 1.3.2 and 1.3.3 were also successfully immobilised into foam and only small amounts of these were washed out, as seen from UV spectra.

Results Hydrophobic and Hydrophilic Response of Nile Red Polymer and Nile Red Polymer Foam The Nile red polymer sample 3.1.1 was placed in deionised water and THF to give the two different environments for the polymer to respond the hydrophobicity. The Nile red in the water responded by having a purple/pink colouration and the Nile red in the THF gave a pink/orange slightly fluorescent solution. This indicates that the Nile red still reacts to changes in the degree of hydrophobicity while co-polymerised with NIPAM. The polymer was also put into ethanol and acetone to show the colour spectrum in different degrees of hydrophobicity, with ethanol being the least hydrophobic and THF being the most hydrophobic environment. This can be seen in FIG. 5.

The foam 3.1.1 was placed in both water and THF and an image of these pieces of foam can be seen in FIG. 6. The foam in water has a purple/blue colour and the foam in the THF has a pink/orange colour, showing that the Nile red polymer is still reactive to different hydrophobicity environments when incorporated/immobilised into the foam.

Example 3.2/Immobilisation of foams

Samples 3.2.1 HBPNIPAM/Vancomycin/NR Copolymer Immobilised Foam

UV of aqueous EtOH washings of Allevyn/HBPNIPAM NR vancomycin showed the immobilisation of vancomycin functionalised polymer. 5 washings were found to be effective in removing residual non-bound polymer (standard protocol).

Example 3.3/Solvent Extraction Aqueous Ethanol

The determination of whether HBPNIPAM/Vancomycin copolymer and HBPNIPAM/Polymyxin copolymer had become immobilised in Allevyn type foam was determined by IR analysis.

1 Method

Sample 3.3.1 HBPNIPAM/Vancomycin Copolymer
1. Hypol (5.13 g) was weighed into a plastic 100 ml beaker and HBPNIPAM/Vancomycin copolymer (0.25 g) was added and they were mixed together thoroughly
2. The mixture was placed in an incubator so that its temperature would reach 38° C.
3. Once the mix was at 38° C. the Brij suspension (4.25 g at 5° C.) was added and the entire mixture was agitated vigorously for 5-6 seconds and then poured into a fresh beaker and allowed to rise
4. After approximately to minutes the foam had cured and was removed from the beaker and dried in an oven overnight (50° C., 48 hours)

Sample 3.3.2 HBPNIPAM/Polymyxin Copolymer

The method was as detailed above. The following quantities were used.

| | |
|---|---|
| HBPNIPAM/Polymyxin copolymer | 0.26 g |
| Hypol | 5.12 g |
| Brij suspension | 4.25 g |

The exhaustive washing of both foams was carried out as in the standard protocol.

The IR results for the two different foams were compared to the control foam and reference spectra for 3.3.1 and 3.3.2. It was seen that there are few differences in the IR spectra for the HBPNIPAM/Vancomycin copolymer foam than to the standard foam. At wavelength numbers 1650 and 1375 cm-1 there were some additional peaks apparent for the HBPNIPAM/Vancomycin copolymer foam these would be in similar places to peaks from the HBPNIPAM/Vancomycin copolymer IR reference. This would suggest that the HBPNIPAM/Vancomycin copolymer had become entrapped within the foam. Stacked plots showed the HBPNIPAM/

Vancomycin copolymer foam IR with the IR of the foam reference subtracted; when compared with the HBPNIPAM/Vancomycin copolymer reference it could clearly be seen that some HBPNIPAM/Vancomycin copolymer had become entrapped within the foam (emphasised by overlay plots).

The HBPNIPAM/Polymyxin copolymer foam was evaluated further using a light microscope (FIG. 7) from which it could be seen that a few strands of the HBPNIPAM/Polymyxin copolymer Sample 3.3.2 were encapsulated within the foam.

A piece of each foam was also exhaustively washed and UV run on each of the washing solutions. It could be seen that for both foams all residues were washed out by the fifth wash, meaning any remaining polymer was entrapped within the foam.

Example 3.4/Solvent Extraction Aqueous Ethanol

Samples
3.4.1 HBPNIPAM/Vancomycin/Nile red (15:1, NIPAM: RAFT) Immobilised foam
3.4.2 HBPNIPAM/Vancomycin/Nile red (25:1, NIPAM: RAFT) immobilised foam
3.4.3 HBPNIPAM/Vancomycin/Nile red (45:1, NIPAM: RAFT) immobilised foam The determination of whether there has been immobilisation of HBPNIPAM/Vancomycin into Allevyn type foam was determined by IP analysis and UV of washing solutions of the foams.

For the control foam the peak of interest is around 284-285 nm, although the lambda max shifts as the absorbency intensity decreases.

It can be seen that with every wash the peak is decreasing in height (/intensity), showing that by wash 5 practically all residues have been washed away from the foam. Results for the HBPNIPAM/Vancomycin/Nile red immobilised foams show that although the peaks of interest start off more intense than with the control foam they are all practically gone by wash 5 for each foam, again showing that all the residue is washed away by wash 5.

IR spectra show a few key differences between the control foam and the foams with immobilised polymer. The most obvious difference is at 1650 $cm^{-1}$. which indicates that the more the ratio of NIPAM: RAFT increases the less polymer appears to be immobilised in the foam. There is also a difference in the IR spectra at 1380 $cm^{-1}$. These differences in the in the IR spectra show that the Vancomycin polymer has become immobilised within the foam.

Example 3.5/Immobilisation of Polymers

Samples
3.5.1 Control foam
3.5.2 HBPNIPAM/Polymyxin copolymer (45:1 NIPAM: RAFT) immobilised foam
3.5.3 HBPNIPAM/Polymyxin copolymer (25:1 NIPAM: RAFT) immobilised foam
3.5.4 HBPNIPAM/Nile red extended outer shell Vancomycin copolymer (15:1 NIPAM:RAFT) immobilised foam
3.5.5 Linear PNIPAM/Vancomycin copolymer (25:1 NIPAM:VBA) immobilised foam
3.5.6 Linear PNIPAM/Vancomycin copolymer (20:1 NIPAM:VBA) immobilised foam All of the samples were washed with 5% aqueous ethanol and UV spectra taken of the washings to determine when the extractable residues had been removed from the foams. It can be seen from the spectra that for each foam by the fifth wash practically all the residues had been washed out. From the spectra there appeared to be no additional residues removed from the functional test foams than there has been from the control foam.

The washed foams were also analysed by IR.

Samples 3.5.2 and 3.5.3 both contained an immobilized copolymer that contained Polymyxin. The IR spectra for these foams and the control foam were compared.

In addition the spectra for sample 3.5.3 (Polymyxin PNIPAM immobilized foam) with the spectra for the control foam subtracted, showing what is truly entrapped within the foam. The peaks for this spectrum correspond to those for the reference Polymyxin and PNIPAM polymer (Farapak), indicating that the functional polymer is entrapped. Spectra were compared for the foams that have Vancomycin functional PNIPAMs incorporated during the foaming process. When compared to the control there is increased signal at 3600-3200 $cm^1$, at 1650 $cm^{-1}$ and 1375 $cm^{-1}$ indicating that the functional PNIPAM has become entrapped within the foam. This is further indicated by looking at comparison spectra for which the control has been subtracted from sample 3.5.5 showing the remaining peaks correspond with those from the reference Vancomycin and reference polymer (Farapak) spectra. This means there is functional PNIPAM within the foam.

Finally the IR spectra of Vancomycin PNIPAM foam samples 3.4.1 to 3.4.3 above were compared to the 3.5.4-6 Vancomycin PNIPAM foams which appear to have a stronger signal at 1650 $cm^{-1}$, possibly meaning that a more concentrated amount of Vancomycin PNIPAM has become entrapped within the foam.

Example 3.6/Solvent Extraction Aqueous Ethanol; Sterilisation

Samples
3.6.1 HBPNIPAM/Vancomycin copolymer (25:1 NIPAM: RAFT) immobilised in polyurethane foam
3.6.2 HBPNIPAM/Polymyxin copolymer (25:1 NIPAM: RAFT) immobilised in polyurethane foam
3.6.3 Linear PNIPAM/Vancomycin copolymer (25:1 NIPAM:VBA) immobilised in polyurethane foam A piece of each of the three sample foams was subject to gamma sterilisation, with another sent to ETOX sterilisation and a third piece kept as a non-sterile comparison. For all three foams it could be seen that sterilisation had no visible effect on the sample colour.

Example

Small pieces of the foam were then placed into a 5% aqueous ethanol solution and acetone; the aqueous ethanol represents a more hydrophilic environment and the acetone a more hydrophobic environment. The hydrophilic environment represents the environment the polymer would be exposed to when there are no bacteria around and the branches of the polymer are open as they would be surrounded by water molecules. The hydrophobic environment is representative of when the polymer is in the presence of bacteria and water molecules are no longer surrounding each branch of the polymer and these branches curl up on themselves.

The foam in ethanol has a purple colour and the foam in acetone has a pink colour, showing that the Nile red polymer is still reactive to different hydrophobicity environments when incorporated/immobilised into the foam.

The linear Vancomycin polymer foam sample 3.6.3 was then examined; the ETOX sterilised samples showed that in two different environments a clear difference in colour is observed with the hydrophilic aqueous ethanol environment causing a purple colour and the hydrophobic acetone environment causing a pink colour. With the gamma sterilised samples the colour changes still occur and appear as strong as for the ETOX samples.

For the ETOX sterilised samples in the two different environments a clear difference in colour was observed with the hydrophilic aqueous ethanol environment causing a purple colour and the hydrophobic acetone environment causing a pink colour with all samples. With the gamma sterilised samples the colour changes still occurred but were not quite as strong as for the ETOX samples.

For the gamma sterilised linear Vancomycin polymer foam sample 3.6.3 the colour changes still occurred and appeared as strong as for the ETOX samples.

Example 3.7—Solvent Extraction Ethanol, Acetone, Dichloromethane

Observation of red coloration of solvent washings and change in red coloration of foams for a number of foams washed in solvents EtOH, acetone, CH2Cl2
25:1 HBPNIPAM/NR/Van/Polymyxin immobilised foam
45:1 HBPNIPAM/NR/Polymyxin immobilised foam (slightly paler and therefore further investigated)
25:1 HBPNIPAM/NR/VAN/Polymyxin immobilised foam (appears unchanged and is representative of no colour change observed with all the other samples).

Tables 1 and 2 show observations of each of the solvents post extraction indicating whether they were clear or coloured. The findings are that all of the samples are clear except for the 45:1 HBPNIPAM/NR/Polymyxin foam which had a pink colouration for all extracting solvents and 45:1 HBPNIPAM/NR/Van foam ethanol extract which was only very slightly pink colour.

An extended extraction was therefore carried out for the 45:1 HBPNIPAM/NR/Polymyxin foam with ethanol for 2 hours then replacing the solvent with fresh ethanol and extracting for another 2 hours so a total of 4 hours extraction. The ethanol after 2 hours was pink coloured as anticipated but the ethanol used for the subsequent 2 hours was clear indicating that no more material could be leached from the foam.

In addition an extended extraction over 2 hours with dichloromethane resulted in the foam still retaining a pink colour with the solvent also taking on a pink colour. Continued washing of this foam with fresh solvent was not carried out, as it was anticipated to also show clear after 4 hours.

Therefore the PNIPAM polymers are quite firmly held within the foam structure. Material extracted from the 45:1 polymer samples is attributed to a greater amount of residual material which would be removed on work up as hereinbefore defined. All foams after extraction including those that were extracted for longer lengths of time remain pink indicating that not all polymer is removed.

TABLE 1

Solvent extraction of PNIPAM/Foam Composites

| Sample Foam | Wt (g) | Ethanol | Wt (g) | Acetone | Wt (g) | CH$_2$Cl$_2$ |
|---|---|---|---|---|---|---|
| 25:1 * HBPNIPAM/NR/Van | 0.28 | Clear | 0.23 | Clear | 0.23 | Clear |

TABLE 1-continued

Solvent extraction of PNIPAM/Foam Composites

| Sample Foam | Wt (g) | Ethanol | Wt (g) | Acetone | Wt (g) | CH$_2$Cl$_2$ |
|---|---|---|---|---|---|---|
| 15:1 HBPNIPAM/NR/Vancomycin | 0.13 | Clear | 0.16 | Clear | 0.12 | Clear |
| 45:1 HBPNIPAM/NR/Vancomycin | 0.16 | Very slightly pink | 0.14 | Clear | 0.15 | Clear |
| 25:1 HBPNIPAM/NR/Polymyxin | 0.13 | Clear | 0.13 | Clear | 0.14 | |
| 45:1 HBPNIPAM/NR/Polymyxin | 0.13 | Pink | 0.12 | Pink | 0.12 | Pink |
| HBPNIPAM/NR/Vancomycin/Polymyxin | 0.14 | Clear | 0.15 | Clear | 0.13 | Clear |

* Wt (g) DMSO Clear

TABLE 2

Solvent extraction of various PNIPAM/Foam Composites

| Sample Foam | Wt (g) | 2 Hr Ethanol Extract | 4 Hr Ethanol Extract | Wt (g) |
|---|---|---|---|---|
| 45:1 HBPNIPAM/NR/Polymyxin** | 0.23 | Pink | Clear | 0.24 |

**2 Hr CH$_2$Cl$_2$ extract pink

Example 3.8 Retention of Polymer in PU Shown by Fluorescence Detection Using LED Powered MLD Device Aim To investigate the retention of P-NIPAM/van/nile red polymers when made into a polyurethane foam dressing.

Materials

25:1 P-NIPAM/van/NR (4% wt in PU foam prepared by the method of Example 2.1.1 and 10% wt in PU foam prepared by the method of Example 2.1.2)

Methods

Images of foam and film dressings were taken using an interfacing device (Excitation with a 580 nm LED array and emission measured with a 647±5 nm band pass filter).

25:1 P-NIPAM/van nile red polyurethane foam were imaged with the device then washed five times in 5% aqueous ethanol. Following the washes the foam was imaged again with the device.

Results

No difference was seen post washing in the fluorescence of the 25:1 P-NIPAM/van nile red (10% wt) foam.

The corresponding 25:1 P-NIPAM van/NR foam (4% wt) following washing showed excellent retention of polymer as shown in FIG. 8. This example clearly shows the retention of polymer in the foam Increased loading of the foam (4% to 10%) with 25:1 P-NIPAM/van/NR polymer resulted in enhanced fluorescence when imaged, as illustrated in FIG. 9.

Example 4

Example 4.1 Polymer Distribution in Polyurethane Foam

Aim

To investigate the distribution of P-NIPAM/van nile red polymer when added to polyurethane foam.

Materials

25:1 P-NIPAM/van/NR (4% wt polymer in PU foam prepared by the method of Example 2.1.1)

Methods

25:1 P-NIPAM/van nile red polyurethane foam was embedded in paraffin wax and 4 □m sections were cut using a microtome. The section was then mounted on a microscope slide. Fluorescence within the foam was visualised using an inverted fluorescent microscope.

Results

Nile red fluorescence (shown as white in FIG. 10) could be seen throughout the histological section of polyurethane foam, however no fluorescence was seen within the voids or pores of the foam section.

Example 4.2 Fluorescence Detection of Polymer in PU Foam Using LED Powered Device Images of foam were taken using a fluorescence excitation and imaging device (Excitation with a 580 nm LED array and emission measured with a 647±5 nm band pass filter).

4.2.1 Thermal Response of Polymer

Aim

To investigate the fluorescent properties of P-NIPAM/van nile red polymers when made into a polyurethane foam or film dressing.

Materials

25:1 P-NIPAM/van/NR (4% wt polymer in PU foam prepared by the method of Example 2.1.1

Methods

Images were taken of foam dressings at various temperatures and post washing 5× with 5% aqueous ethanol.

Results

25:1 P-NIPAM/van nile red polymer in polyurethane foam was incubated at 4° C., room temperature, and 50° C. alongside polyurethane foam without polymer (Control). The foam was then imaged using the excitation and imaging device and an increase in fluorescence saturation (blue pixels) could be clearly seen when increasing temperature. This result suggested that the polymer was still capable of undergoing a thermoresponsive coil-to-globule transition Results are shown in FIGS. 11-13.

Example 4.2.2 Fluorescent Activity of Dressing Comprising Polymer in PU Foam Supported on Adhesive Film Aim To investigate the ability to detect fluorescence of P-NIPAM/van/nile red polymers when made into a polyurethane foam dressing.

Materials

Island Dressing comprising 25:1 P-NIPAM/van/NR in PU foam (prepared by the method of Example 2.1.1) supported on OPSITE adhesive film Methods The material was imaged Results The results in FIG. 14 show excellent imaging of fluorescence of the material.

Example 4.4 Binding of Bacteria by Polymer in PU Film Shown by Fluorescence Detection Aim To investigate the binding of bacteria by P-NIPAM/van/nile red polymers when made into a polyurethane film dressing.

Materials

25:1 P-NIPAM/COOH/NR (polymer in PU film)

Methods

25:1 P-NIPAM/COOH nile red polymer (1.5.2) was cast into a polyurethane film. Using the interfacing device it was possible to image the fluorescence from nile red and this appeared to show some increase with temperature. Fluorescence was also measured over 30 minutes as the temperature of the film was increased from 4° C. to 42° C. using a fluorescent plate reader as described above.

Results

This result shown in FIG. 15 suggests that the polymer within the film is thermoresponsive and capable of undergoing a coil-to-globule transition.

Example 5—Bacterial Binding and Indication

5.1 Selective Binding of Bacteria (by Gram Type) by Polymer (by Degree of Branching) in PU Shown by Fluorescence Detection Aim To investigate the binding of bacteria by P-NIPAM/van/nile red polymers when made into a polyurethane foam dressing.

Materials

25:1 P-NIPAM/van/NR (polymer in PU foam prepared by the method of Example 2.1.1)

15:1 P-NIPAM/van/NR (polymer in PU foam prepared by the method of Example 2.1.1)

Linear extended P-NIPAM/van/NR (polymer in PU foam prepared by the method of Example 2.1.1)

Hyperbranched extended P-NIPAM/van/NR (polymer in PU foam prepared by the method of Example 2.1.1)

Methods

25:1, 15:1, Linear-Extended, and Hyperbranched-Extended P-NIPAM/van nile red polyurethane foam samples were cultured with either PBS, *S. aureus* or *P. aeruginosa* for 30 minutes. Fluorescent readings were taken using a Tecan M200 plate reader every 60 seconds. Foam fluorescence varied substantially at the beginning of the experiment due to variation in thickness and porosity and therefor fold change in fluorescence between 2 minutes and 15 minutes was used to determine if an effective response to *S. aureus* had occurred.

Results

25:1, 15:1 and HB-ext P-NIPAM/van nile red foam dressings had a positive fold change when cultured with *S. aureus* but not *P. aeruginosa*, suggesting that these dressings are responding to the bacteria in a similar manner to the soluble polymer.

Example 5.2 Bacterial Growth Inhibition

Aim

To test whether P-NIPAM/van nile red polymer is bactericidal

To demonstrate that P-NIPAM/van nile red polymer does not release van

Materials

25:1 P-NIPAM/van/NR (prepared by the method of Example 2.1.1)

Method

*S. aureus* was spread on a brain heart infusion agar plate (1) so as to cover the entire plate with a lawn of bacteria (2).

Three 10 µl drops of vancomycin (1 mg/ml) (4) were dispensed on one side of the plate as a positive control for bacterial inhibition and three 10 µl drops of 25:1 P-NIPAM/van nile red polymer after washing (3) were added to the plate on the other side. The plate was then incubated at 37° C. overnight.

Results

Following overnight incubation, growth inhibition of *S. aureus* was clearly visible where the drops of vancomycin (4) had been placed whereas there was no visible growth inhibition from the drops of 25:1 P-NIPAM/van nile red polymer (3).

The results are shown in FIG. 17 illustrating agar plate (1) having lawn of bacteria (2) with drops of vancomycin (4) and drops of 25:1 P-NIPAM/van nile red polymer after washing (3).

Example 5.3 Non Bactericidal Activity of Polymer in PU Foam Shown by Bacterial Recovery after Binding Aim To investigate the non-bactericidal activity of polymer in PU foam by recovery of live bacteria after binding by P-NIPAM/van/nile red polymers when made into a polyurethane foam dressing.

Materials

25:1 P-NIPAM/van/NR (polymer in PU foam prepared by the method of Example 2.11.)

Methods

Additional graphs/images

Results

FIG. 18 shows recovery of bacteria from 15:1 P-NIPAM/van corresponding to that from PBS. The polymer in foam is concluded to be non-bactericidal.

Example 5.4 Binding of Bacteria by Polymer in PU Shown by Fluorescence Detection Aim To investigate the binding of bacteria by P-NIPAM/van/nile red polymers when made into a polyurethane foam dressing.

Materials

25:1 P-NIPAM/van/NR (polymer in PU foam prepared by the method of Example 2.1.1)

Methods

Binding of *S. aureus* to 25:1 P-NIPAM/van nile red polyurethane foam was evaluated following a 24 hour incubation of bacteria with foam at 37° C. Foam was then embedded in paraffin wax and 4 µm sections were cut using a microtome. The sections were mounted on a microscope slide and xylene was used to remove the wax. The sections were then Gram stained to highlight bacteria. Sections were imaged using an upright brightfield microscope with a 20× magnification lens.

Results

The Results are illustrated in FIG. 19. Vast amounts of *S. aureus* (dark violet cocci) could be seen attached to the foam, particularly on the edges

Example 5.5—Gram Staining of Foams Incubated with Bacteria

Aim

To investigate the selective binding of Gram positive and Gram negative bacteria by P-NIPAM/van/nile red and P-NIPAM/poly/nile red polymers when made into a polyurethane foam dressing.

Materials

P-NIPAM/van/NR (polymer in PU foam prepared by the method of Example 2.1.1)

Methods

Using the method of Example 5.4

Vancomycin-HB-PNIPAM based polymer and the Polymyxin-HB-PNIPAM based polymer have both been incorporated into polyurethane foam, which can easily be incorporated into any foam based dressing.

Results

The two polymers have been shown to react differently to Gram positive and Gram negative bacteria. Example images can be seen in FIG. 20 to FIG. 23, where FIG. 20 shows a Gram stain of the control foam (no polymer present) with staph *aureus* (Gram positive bacterium). FIG. 21 shows the Vancomycin nile red polymer immobilised in foam in PBS (phosphate buffer solution), FIG. 22 the foam has been incubated with *pseudomonas aeruginosa* (Gram negative bacteria) it can be seen that there is no difference between FIG. 21 and FIG. 22, meaning there has been no capture of the bacteria onto the foam. Whereas in FIG. 23 the Vancomycin nile red polymer immobilised in foam has been incubated with Staph *aureus*, black particles can be seen on the foam showing that the Gram positive bacteria has been captured by the polymer in the foam.

The example illustrates the advantages of the described invention, in relation to the ability to detect whether bacteria is Gram positive or Gram negative.

The invention claimed is:

1. A polymeric material comprising a semi-interpenetrating network of a polyurethane and a hydrophilic polymer, wherein the hydrophilic polymer comprises:
   a first moiety for binding to species, wherein hydrophilicity of the hydrophilic polymer is changed when the species is bound to the first moiety;
   a second moiety comprising a solvatochromic dye which changes color in response to the change in the hydrophilicity of the hydrophilic polymer; and
   wherein the first moiety and the second moiety are covalently bonded to the hydrophilic polymer.

2. The material of claim 1, wherein the species are selected from the group consisting of proton, ion, bacteria, yeast, fungus, and combinations thereof.

3. The material of claim 1, wherein said first and second moieties are immobilised in the semi-interpenetrating network and are not leached from the polymer material.

4. The material of claim 1, wherein said first moiety comprises antibiotic or derivative thereof, and the antibiotic is modified and/or immobilised to be devoid of antibiotic activity.

5. The material of claim 1, wherein the polymeric material is provided as a sheet or as a shaped object.

6. The material of claim 1, wherein the hydrophilic polymer comprises a polymer selected from the group consisting of polyacrylamide, polyalkyl acrylamide, polyallyl acrylamide, polyacrylic acid, polymethacrylic acid, and copolymers thereof, wherein alkyl is ethyl, propyl, or butyl.

7. The material of claim 6, wherein the hydrophilic polymer comprises poly(N-isopropyl acrylamide) (PNIPAM).

8. The material of claim 1, wherein the solvatochromatic dye changes wavelength or intensity of fluorescence in response to the change in the hydrophilicity of the hydrophilic polymer.

9. The material of claim 1, wherein the material is provided in the form of foam, or of a film, perforated film, membrane, water impermeable membrane providing moisture vapour transmission (MVT), adhesive layer or coating, sheet, block, non-woven or woven fabric, thread, ribbon or combinations thereof.

10. The material of claim 1, wherein said first moiety is selected from the group consisting of acid or base groups, peptide antibiotics and their derivatives, non-peptide antibiotics and their derivatives, antibody fragments, peptide sequences, oligo- and mono-saccharides, and combinations thereof.

11. The material of claim 1, wherein the solvatochromic dye is selected from the group consisting of Nile Red, Nile Blue, Dansyl or derivatives thereof.

12. The material of claim 1, wherein the hydrophilic polymer changes from an open coil configuration to a globular configuration at a body temperature when the species bind to the first moiety.

* * * * *